(12) United States Patent
King et al.

(10) Patent No.: US 7,928,343 B2
(45) Date of Patent: Apr. 19, 2011

(54) MICROCANTILEVER HEATER-THERMOMETER WITH INTEGRATED TEMPERATURE-COMPENSATED STRAIN SENSOR

(75) Inventors: William P. King, Champaign, IL (US); Jungchul Lee, Champaign, IL (US); Fabian T. Goericke, Wolfsburg (DE)

(73) Assignee: The Board of Trustees of the University of Illinois, Urbana, IL (US)

( * ) Notice: Subject to any disclaimer, the term of this patent is extended or adjusted under 35 U.S.C. 154(b) by 498 days.

(21) Appl. No.: 11/950,029

(22) Filed: Dec. 4, 2007

(65) Prior Publication Data
US 2009/0139340 A1 Jun. 4, 2009

(51) Int. Cl.
H05B 3/22 (2006.01)
H05B 3/68 (2006.01)
G01L 1/22 (2006.01)
G01L 19/04 (2006.01)
G01L 1/26 (2006.01)

(52) U.S. Cl. ............... 219/444.1; 73/766; 219/446.1
(58) Field of Classification Search ............ 73/766; 219/444.1, 446.1–448.11, 448.13–448.14, 219/448.17
See application file for complete search history.

(56) References Cited

U.S. PATENT DOCUMENTS

| | | | |
|---|---|---|---|
| 4,166,269 A | 8/1979 | Stephens et al. | |
| 5,345,815 A | 9/1994 | Albrecht et al. | |
| 5,386,720 A | 2/1995 | Toda et al. | |
| 5,441,343 A | 8/1995 | Pylkki et al. | |
| 5,444,244 A | 8/1995 | Kirk et al. | |
| 5,451,371 A | 9/1995 | Zanini-Fisher et al. | |
| 5,464,966 A * | 11/1995 | Gaitan et al. | 219/544 |
| 5,583,286 A | 12/1996 | Matsuyama | |
| 5,801,070 A | 9/1998 | Zanini-Fisher et al. | |
| 5,929,438 A | 7/1999 | Suzuki et al. | |
| 5,936,237 A | 8/1999 | van der Weide | |
| 5,969,238 A | 10/1999 | Fischer | |
| 6,050,722 A * | 4/2000 | Thundat et al. | 374/121 |
| 6,073,485 A | 6/2000 | Kitamura | |
| 6,094,971 A | 8/2000 | Edwards et al. | |
| 6,096,559 A * | 8/2000 | Thundat et al. | 436/147 |
| 6,097,197 A | 8/2000 | Matsuyama et al. | |
| 6,383,823 B1 | 5/2002 | Takahashi et al. | |
| 6,436,346 B1 | 8/2002 | Doktycz et al. | |
| 6,452,170 B1 | 9/2002 | Zypman et al. | |

(Continued)

FOREIGN PATENT DOCUMENTS
WO   WO 9410822 A1 *   5/1994
(Continued)

OTHER PUBLICATIONS

P.J. French, "Polysilicon: a versatile material for microsystems", 2002, Sensors and Actuators A, 99, pp. 3-12.*

(Continued)

*Primary Examiner* — Thomas P Noland
(74) *Attorney, Agent, or Firm* — Greenlee Sullivan P.C.

(57) ABSTRACT

The present invention provides microcantilever hotplate devices which incorporate temperature compensating strain sensors. The microcantilever hotplate devices of the present invention comprise microcantilevers having temperature compensating strain sensors and resistive heaters. The present invention also provides methods for using a microcantilever hotplate for temperature compensated surface stress measurements, chemical/biochemical sensing, measuring various properties of compounds adhered to the microcantilever hotplate surface, or for temperature compensated deflection measurements.

22 Claims, 11 Drawing Sheets

U.S. PATENT DOCUMENTS

| | | | |
|---|---|---|---|
| 6,467,951 | B1 | 10/2002 | Ghoshal |
| 6,487,515 | B1 | 11/2002 | Ghoshal |
| 6,535,824 | B1* | 3/2003 | Mansky et al. ............. 506/8 |
| 6,583,412 | B2 | 6/2003 | Williams |
| 6,667,467 | B2 | 12/2003 | Shimizu et al. |
| 6,762,402 | B2 | 7/2004 | Choi et al. |
| 6,763,705 | B1 | 7/2004 | Thundat et al. |
| 6,785,041 | B1 | 8/2004 | Vodopyanov |
| 6,893,884 | B2 | 5/2005 | Shi et al. |
| 6,894,272 | B2 | 5/2005 | Kranz et al. |
| 6,930,502 | B2 | 8/2005 | Lee et al. |
| 6,932,504 | B2 | 8/2005 | Takahashi et al. |
| 6,935,167 | B1 | 8/2005 | Sahin et al. |
| 7,033,840 | B1 | 4/2006 | Tagge et al. |
| 7,038,996 | B2 | 5/2006 | Binnig et al. |
| 7,074,340 | B2 | 7/2006 | Lugstein et al. |
| 7,155,964 | B2 | 1/2007 | Huang et al. |
| 7,168,298 | B1* | 1/2007 | Manginell et al. ........ 73/54.25 |
| 7,208,730 | B2 | 4/2007 | Berstis |
| 7,211,789 | B2 | 5/2007 | Berstis |
| 7,260,980 | B2* | 8/2007 | Adams et al. ............. 73/31.05 |
| 7,261,461 | B2* | 8/2007 | Grudin et al. ............... 374/43 |
| 7,268,348 | B2 | 9/2007 | Binning et al. |
| 7,281,419 | B2 | 10/2007 | Wang et al. |
| 7,291,466 | B2 | 11/2007 | Su et al. |
| 7,404,314 | B2 | 7/2008 | Sahin et al. |
| 7,451,638 | B1 | 11/2008 | Sahin et al. |
| 7,521,257 | B2* | 4/2009 | Adams et al. ............. 436/183 |
| 2003/0101006 | A1 | 5/2003 | Mansky et al. |
| 2004/0195096 | A1 | 10/2004 | Tsamis et al. |
| 2004/0223884 | A1* | 11/2004 | Chen et al. .................. 422/88 |
| 2004/0228258 | A1 | 11/2004 | Binnig et al. |
| 2005/0109081 | A1 | 5/2005 | Zribi et al. |
| 2005/0127926 | A1 | 6/2005 | Lee et al. |
| 2005/0164299 | A1* | 7/2005 | Stewart ..................... 435/7.1 |
| 2006/0032289 | A1* | 2/2006 | Pinnaduwage et al. ...... 73/25.05 |
| 2006/0040057 | A1 | 2/2006 | Sheehan et al. |
| 2006/0150720 | A1 | 7/2006 | Nakayama et al. |
| 2006/0207317 | A1 | 9/2006 | Watanabe |
| 2006/0222047 | A1 | 10/2006 | Reading |
| 2006/0238206 | A1 | 10/2006 | Eng et al. |
| 2006/0254345 | A1 | 11/2006 | King et al. |
| 2007/0063141 | A1 | 3/2007 | Duerig et al. |
| 2007/0109091 | A1* | 5/2007 | Landsberger et al. ......... 338/25 |
| 2007/0114401 | A1 | 5/2007 | King et al. |
| 2007/0125753 | A1 | 6/2007 | Fink et al. |
| 2007/0189920 | A1 | 8/2007 | Gimzewski |
| 2007/0190562 | A1 | 8/2007 | Berstis |
| 2007/0286254 | A1 | 12/2007 | Fon et al. |
| 2008/0093226 | A1* | 4/2008 | Briman et al. ............. 205/775 |
| 2008/0283755 | A1 | 11/2008 | Dazzi et al. |
| 2008/0295583 | A1 | 12/2008 | Giessibl |
| 2009/0013770 | A1 | 1/2009 | Proksch et al. |
| 2009/0139340 | A1 | 6/2009 | King et al. |
| 2009/0249521 | A1 | 10/2009 | Dazzi et al. |

FOREIGN PATENT DOCUMENTS

| | | |
|---|---|---|
| WO | WO 03/011747 | 2/2003 |
| WO | WO 2006/046924 | 5/2006 |
| WO | WO 2006/073426 | 7/2006 |
| WO | WO 2006/107991 | 11/2006 |
| WO | WO 2007/011364 | 1/2007 |
| WO | WO 2007/026177 | 3/2007 |
| WO | WO 2008/143817 | 11/2008 |
| WO | WO 2009/097487 | 8/2009 |
| WO | WO 2010/022285 | 2/2010 |

OTHER PUBLICATIONS

Abedinov et al. (2001) "Micromachined Piezoresistive Cantilever Array With Integrated Resistive Microheater for Calorimetry and Mass Detection," *J. Vac. Sci Technol. A* 19(6):2884-2888.

Abel et al. (Jun. 2007) "Thermal Metrology of Silicon Microstructures Using Raman Spectroscopy," *IEEE Trans. Comp. Pack. Tech.* 30(2):200-208.

Akiyama et al. (2000) "Integrated Atomic Force Microscopy Array Probe with Metal-Oxide-Semiconductor Field Effect Transistor Stress Sensor, Thermal Bimorph Actuator, and On-Chip Complementary Metal-Oxide-Semiconductor Electronics," *J. Vac. Sci. Technol. B* 18(6):2669-2675.

Berger et al. (Jul. 1, 1996) "Thermal Analysis Using a Micromechanical Calorimeter," *Appl. Phys. Lett.* 69(1):40-42.

Binning et al. (Mar. 3, 1986) "Atomic Force Microscope," *Phys. Rev. Lett.* 56(9):930-933.

Biswal et al. (2006) "Nanomechanical Detection of DNA Melting on Microcantilever Surfaces," *Anal. Chem.* 78:7104-7109.

Biswal et al. (2007) "Using a Microcantilever Array for Detecting Phase Transitions and Stability of DNA," *Clin. Lab. Med.* 27:163-171.

Boisen et al. (2000) "Environmental Sensors Based on Micromachined Cantilevers with Integrated Read-Out," *Ultramicroscopy* 82:11-16.

Chui et al. (Mar. 1998) "Low-Stiffness Silicon Cantilevers with Integrated Heaters and Piezoresistive Sensors for High-Density AFM Thermomechanical Data Storage," *J. Microelectrmech. Syst.* 7(1):69-78.

Chui et al. (2007) "Advanced Temperature Compensation for Piezoresistive Sensors Based on Crystallographic Orientation," *Rev. Sci. Instrum.* 78:043706.

Despont et al. (2000) "VLSI-NEMS Chip for Parallel AFM Data Storage," *Sens. Actuators A* 80:100-107.

Goericke et al. (2007) "Microcantilever Hotplates with Temperature-Compensated Peizoresistive Strain Sensors," *Sens. Actuators A* 143(2):181-190.

Hagleitner et al. (Nov. 15, 2001) "Smart Single-Chip Gas Sensor Microsystem," *Nature* 414:293-296.

Hull (1999) "Electrical Properties," and "Implantation/ Irradiation of Silicon," In; *Properties of Crystalline Silicon*, Ch. 8 and 14, INSPEC, London pp. 411-475 and 731-773.

Jensenius et al. (May 1, 2000) "A Microcantilever-Based Alcohol Vapor Sensor-Application and Response Model," *Appl. Phys. Lett.* 76(18):2615-2617.

Kim et al. (2007) "Nanotopographical Imaging Using a Heated Atomic Force Microscope Cantilever Probe," *Sens. Actuators A* 136:95-103.

King et al. (Dec. 2002) "Design of Atomic Force Microscope Cantilevers for Combined Thermomechanical Writing and Thermal Reading in Array Operation," *J. Microelectromech. Syst.* 11(6):765-774.

King et al. (2006) "Nanoscale Thermal Analysis of an Energetic Material," *Nano Lett.* 6(9):2145-2149.

Lee et al. (Dec. 2006) "Electrical, Thermal, and Mechanical Characterization of Silicon Microcantilever Heaters," *J. Microelectromech. Syst.* 15(6):1644-1655.

Lee et al. (2007) "Characterization of Liquid and Gaseous Micro- and Nanojets using Microcantilever Sensors," *Sens. Actuators A* 134:128-139.

Lee et al. (2007) "Microcantilever Hotplates: Design, Fabrication, and Characterization," *Sens. Actuators A* 136:291-298.

Lutwyche et al. (1999) "5×5 2D AFM Cantilever Arrays a First Step Towards a Terabit Storage Device," *Sens. Actuators A* 73:89-94.

Madou (1997) "Wet Bulk Micromachining," and "Microfabrication Applications," In *Fundamentals of Microfabriation*, Ch. 4 and 10, CRC Press, Boca Raton, Florida, pp. 145-215 and 449-514.

Marie et al. (2002) "Adsorption Kinetics and Mechanical Properties of Thiol-Modified DNA-oligos on Gold Investigated by Microcantilever Sensors," *Ultramicroscopy* 91:29-36.

Nelson et al. (2006) "Direct Deposition of Continuous Metal Nanostructures by Thermal Dip-Pen Nanolithography," *Appl. Phys. Lett.* 88:033104.

Nelson et al. (2007) "Measuring Material Softening with Nanoscale Spatial Resolution Using Heated Silicon Probes," *Rev. Sci. Instrum.* 78:023702.

Nelson et al. (2007) "Temperature Calibration of Heated Silicon Atomic Force Microscope Cantilevers," *Sens. Actuators A* 140:51-59.

Park et al. (2007) "Topography Imaging with a Heated Atomic Force Microscope Cantilever in Tapping Mode," *Rev. Sci. Instrum.* 78:043709.

Pedrak et al. (2003) "Micromachined Atomic Force Microscopy Sensor with Integrated Piezoresistive Sensor and Thermal Bimorph Actuator for High-Speed Tapping-Mode Atomic Force Microscopy Phase-Imaging in Higher Eigenmodes," *J. Vac. Sci. Technol. B* 21(6):3102-3107.

Pinnaduwage et al. (Oct. 2, 2003) "A Microsensor for Trinitoluene Vapour," *Nature* 425:474.

Rasmussen et al. (2003) "Optimized Cantilever Biosensor with Piezoresistive Read-Out," *Ultramicroscopy* 97:371-376.

Roylance et al. (Dec. 1979) "A Batch-Fabricated Silicon Accelerometer," *IEEE Trans. Elec. Dev.* 26(12):1911-1917.

Su et al. (2002) "Characterization of a Highly Sensitive Ultra-Thin Piezoresistive Silicon Cantilever Probe and Its Application in Gas Flow Velocity Sensing," *J. Micromech. Microeng.* 12:780-785.

Sunden et al. (2006) "Room-Temperature Chemical Vapor Deposition and Mass Detection on a Heated Atomic Force Microscope Cantilever," *Appl. Phys. Lett.* 88:033107.

Thundat et al. (May 23, 1994) "Thermal and Ambient-Induced Deflections of Scanning Force Microscope Cantilevers," *Appl. Phys. Lett.* 64(21):2894-2896.

Thundat et al. (Mar. 27, 1995) "Detection of Mercury Vapor Using Resonating Microcantilevers," *Appl. Phys. Lett.* 66(13):1695-1697.

Tortonese et al. (Feb. 22, 1993) "Atomic Resolution with an Atomic Force Microscope Using Piezoresistive Detection," *Appl. Phys. Lett.* 62(8):834-836.

Triantafyllopoulou et al. (2006) "Alternative Micro-Hotplate Design for Low Power Sensor Arrays," *Microelectron. Eng.* 83:1189-1191.

Yang et al. (2006) "Nano-Mechanical Electro-Thermal Probe Array Used for High-Density Storage Based on NEMS Technology," *Microelec. Reliability* 46:805-810.

Albright et al. (Apr. 1999) "'True' Temperature Measurements on Microscope Semiconductor Targets," In; SPIE Conference on Thermosense XXI, Orlando Florida, SPIE 3700:245-250.

Allen et al. (1998) "MEMS-Based Scanning Calorimeter for Thermodynamic Properties of Nanostructures," *Microscale Thermophys. Eng.* 2:11-19.

Beckel et al. (Mar. 30, 2007) "Micro-Hotplates—A Platform for Micro-Solid Oxide Fuel Cells," *J. Power Source* 166:143-148.

Belmonte et al. (Apr. 26, 2006) High-Temperature Low-Power Performing Micromachined Suspended Micro-Hotplate for Gas sensing Applications, *Sens. Actuators B. Chem.* 114:826-835.

Berger et al. "Micromechanical Thermogravimetry," *Chem. Phys. Lett.* 294:363-369, Sep. 1998.

Beyder et al. (2006) "Reducing Probe Dependent Drift in Atomic Force Microscope with Symmetrically Supported Torsion Levers," *Rev. Sci Instrum.* 77:0056105, 3 pages.

Binnig et al. (Mar. 1, 1999) "Ultrahigh-Density Atomic Force Microscopy Data Storage with Erase Capability," *Appl. Phys. Lett.* 74(9):1329-1331.

Biswal et al. (Aug. 2006) "Using a Microcantilever Array for Detecting Phase Transitions and Stability of DNA," *J. Assoc. Lab. Auto.* 11:222-226.

Brown et al. (1999) "Cantilever-in-Cantilever Micromachined Pressure Sensors Fabricated in CMOS Technology," *Proc. 1999 IEEE Can. Conf. On Elec. and Comp. Eng.* :1686-1691, conference held May 1999.

Butt et al. (1995) "Calculation of Thermal Noise in Atomic Force Microscopy," *Nanotechnology* 6(1):1-7.

Cavicchi et all. (Jan. 1, 2004) "Micro-Differential Scanning Calorimeter for Combustible Gas Sensing," *Sens. Actuators B. Chem.* 97:22-30.

Chen et al. (Aug. 1994) "Resonance Response of Scanning Force Microscopy Cantilevers," *Rev. Sci. Instrum.* 65(8):2532-2537.

Chui et al. (1999) "Intrinsic Carrier Thermal Runaway in Silicon Microcantilevers," *Microscale Thermophys. Eng.* 3:217-228.

Chui et al. "Low Stiffness Silicon Cantilevers for Thermal Writing and Peizoresistive Readback with Atomic Force Microscope," *Appl. Phys. Lett.* :2767-2769, vol. 69, No. 18, Oct. 1996.

Datskos (1996) "Remote Infrared Radiation Detection Using Piezoresistive Microcantilevers," *Appl. Phys. Lett.* 69: 2986-2988 , vol. 69, No. 11, Nov. 1996.

Dazzi et al. (2007) "Analysis of Nano-Chemical Mapping Performed by an AFM-Based ("AFMIR") Acousto-Optic Technique," *Ultramicroscopy* 107(12):1194-1200.

Dazzi et al. "Local Infrared Microspectroscopy with Subwavelength Spatial Resolution with an Atomic Force Microscope Tip used as a Photothermal Sensor," *Optics Lett.* 30(18):2388-2390 , Sep. 2005.

Dazzi et al. (2006) "Subwavelength Infrared Spectromicroscopy using an AFM as a Local Absorption Sensor," *Infrared Phys. Technol.* 49:113-121.

Dazzi et al. (2004) "Theoretical Study of an Absorbing Sample in Infrared Near-Field Spectromicroscopy," *Optics Comm.* 235:351-360.

Dazzi (2008) "Sub-100nm Infrared Spectroscopy and Imaging based on a near-field photo-thermal technique ("PTIR")," Biomedical vibrational spectroscopy, J. Wiley ed., 291, 23 pages.

Degamber et al. (Sep. 2004) "Simultaneous DSC/FTIRS/TMA," *Meas. Sci. Technol.* 15:L5-L10.

Denlinger et al. (Apr. 1994) "Thin-Film Microcalorimeter for Heat-Capacity Measurements from 1.5K to 800K," *Rev. Sci.* 5:946-958, vol. 65 , No. 4.

Drechsler et al. (2003) "Cantilevers with Nano-Heaters for Thermomechanical Storage Application," *Microelectr. Eng.* 67/68:397-404.

Dücsö et al. (May 1997) "Porous Silicon Bulk Micromachining for Thermally Isolated Membrane Formation," *Sens. Actuators A Phys.* 60:235-239.

Efremov et al. (Feb. 26, 2002) "Thin-Film Differential Scanning Calorimetry: A New Probe for Assignment of the Glass Transition of Ultrathin Polymer Films," *Macromolecules* 1481-1483, vol. 35, No. 5.

Efremov et al. (Aug. 22, 2003) "Glass Transition in Ultrathin Polymer Films: Calorimetric Study," *Phys. Rev. Lett.* 91(8):085703 , 4 pages.

Efremov et al. (Jun. 26, 2003) "Glass Transition of Thin Films of Poly(2-Vinyl Pyridine) and Poly(Methyls Methacrylate): *Nanocalorimetry Measurements" Thermochim Acta* 403:37-41.

Efremov et al. (Jun. 15, 2004) "Probing Glass Transition of Ultrathin Polymer Films at a Time Scale of Seconds Using Fast Differential Scanning Calorimetry," *Macromolecules* 37:4607-4616.

Efremov et al. (2004) "Ultrasensitive, Fast, Thin-Film Differential Scanning Calorimeter," *Rev. Sci Instrom.* 75:179-191, vol. 75, No. 1, Jan. 2004.

Felts et al. (2009) "Mechanical Design for Tailoring Resonance Harmonics of an Atomic Force Microscope Cantilever During Tip-Surface Contact," *J. Micromech. Microeng.* 19: 115008, 6 pages.

Fernando et al. "Improved Cantilever Profiles for Sensor Elements," *J. Phys. D-Appl. Phys.* 40(24):7652-7655, Nov. 2007.

Frisbie et al. "Functional Group Imaging by Chemical Force Microscopy," *Science* 265:2071-2074, Sep. 1994.

Fritz et al. "Translating Biomolecular Recognition into Nanomechanics," *Science* 288:316-318, Apr. 2000.

Fung et al. (Jun. 1996) "Thermal Analysis and Design of a Micro-Hotplate for Integrated Gas-Sensor Applications," *Sens. Actuators a Phys.* 54:482-487.

Fürjes et al. (Apr. 30, 2002) "Thermal Investigation of Micro-Filament Heaters," *Sens. Actuators A. Phys.* 99:98-103.

Fürjes et al. (2004) "Thermal Characterization of Mico-Hotplates Used in Sensor Structures," *Superlattices Microstruct.* 35:455-464, available online Jun. 2004.

Fürjes et al. (Jul. 2002) "Materials and Processing for Realization of Micro-Hotplates Operated at Elevated Temperature," *J. Micromech. Microeng.* 12:425-429.

Gimzewski et al. (1994) "Observation of a Chemical Reaction Using a Micromechanical Sensor," *Chem. Phys. Lett.* 217:589-594, vol. 217, Nos. 5,6, Jan. 1994.

Gotsmann et al. (2005) "Experimental Observation of Attractive and Repulsive Thermal Forces on Microcantilevers," Appl. Phys. Lett. 87:194102, 3 pages, pub. online Oct. 2005.

Gotsmann et al. (2004) "Thermally Activated Nanowear Models of a Polymer Surface Induced by a Heated Tip," *Langmuir* 20:1495-1500, vol. 20, No. 4, pub. on Web Jan. 2004.

Graf et al. (Jan. 2005) "3D Nonlinear Modeling of Microhotplates in CMOS Technology for Use as Metal-Oxide-Based Gas Sensors," *J. Micromech. Microeng.* 15:190-200.

Gruverman "Scanning Force Microscopy for the Study of Domain Structure in Ferroelectric Thin Films," *J. Vac. Sci. Technol. B: Microelectron. Nanometer Struct.* 14(2):602-605, Mar./Apr. 1996.

Guo et al. (Jan. 2007) "A Monolithic Integrated 4x4 Tin Oxide Gas Sensor Array with On-Chip Multiplexing and Differential Readout Circuits," *Solid-State Electron.* 51:69-76.

Han et al. (May 17, 2005) "Size Effect on Heat Transfer in Micro Gas Sensors," *Sens. Actuators A Phys* 120:397-402.

Han et al. (2005) "A Novel Temperature-Compensating Structure for Micromechanical Bridge Resonator," *J. Micromech. Microeng.* 15: 702-705.

Hey et al. (1997) "A Combined Differential Scanning Calorimeter Optical Video Microscope for Crystallization Studies," *J. Therm. Anal.* 49:991-998.

Hodges "Improved Atomic Force Microscope Cantilever Performance by Ion Beam Modification," *Rev. Sci. Instrum.* 72(10):3880-3883, Oct. 2001.

Holbery et al. (2000) "Experimental Determination of Scanning Probe Microscope Cantilever Spring Constants Utilizing a Nanoindentation Apparatus," *Rev. Sci. Instrum.* 71(10):3769-3776, Oct. 2000.

Hotovy et al. (Apr. 2008) "Gallium Arsenide Suspended Microheater for MEMS Sensor Arrays," *Microsyst. Tech.* 14:629-635.

Hsu et al. "Cubic AgPbmSbTe2+m: Bulk Thermoelectric Materials with High Figure of Merit," *Science* 303:818-821, Feb. 2004.

Hu et al. (2008) "Investigation of the Natural Convection Boundary Condition in Microfabricated Structures," *Int. J. Therm. Sci.* 47:820-824, availableOnlineAug-07.

Hutter et al. "Calibration of Atomic-Force Microscope Tips," *Rev. Sci. Instrum.* vol. 64, No. 7, pp. 1868-1873, Jul. 1993.

International Search Report and Written Opinion, Corresponding to International Application No. PCT/US09/32545, Mailed Apr. 9, 2009.

International Search Report and Written Opinion, Corresponding to International Application No. PCT/US09/54539, Mailed Dec. 23, 2009.

Johnson et al. (Jan. 17, 1992) "Applications of Simultaneous Dsc Ftir Analysis," *Thermochim. Acta* 195:5-20.

Kim et al. (Jun. 2009) "Thermal Conduction Between a Heated Microcantilever and a Surrounding Air Environment," *Appl. Therm. Eng.* 29(8-9):1631-1641.

King et al. (Feb. 26, 2001) "Atomic Force Microscope Cantivers for Combined Thermomechanical Data Writing and Reading," *Appl. Phys. Lett.* 78(9):1300-1302.

Krebs et al. (1993) "A Low-Power Integrated Catalytic Gas Sensor," *Sens. Actuators B* 13/14:155-158.

Laconte et al. (Oct. 2004) "SOI CMOS Compatible Low-Power Microheater Optimization for the Fabrication of Smart Gas Sensors," *IEEE Sens J.* 4(5):670-680.

Lai et al. (Aug. 28, 1995) "High-Speed ($10^4$ °C/S) Scanning Microcalorimetry with Monolayer Sensitivity (J/m2)," *Appl. Phys. Lett.* 1229-1231, vol. 67, No. 9.

Lai et al. (Jul. 1, 1996) "Size-Dependent Melting Properties of Small Tin Particles: Nanocalorimetric Measurements," *Phys. Rev. LEtt.* 99-102, vol. 77, No. 1.

Lai et al. (Mar. 2, 1998) "Melting Point Depression of Al Clusters Generated During the Early Stages of Film Growth: Nanocalorimetry Measurements," *Appl. Phys. Lett.* 1098-1100, vol. 72, No. 9.

Lee et al.(2003) "Classifying Combustible Gases Using Microgas Sensor Array," *Sens. Actuators B* 93:1-6.

Lee, J. (May 2007) "Fabrication, Characterization and Application of Multifunctional Microcantilever Heaters," Ph.D. Dissertation, Georgia Institute of Technology, 203 pages, available online Mar. 2008.

Lee et al. (2008) "Microthermogravimetry Using a Microcantilever Hot Plate with Integrated Temperature-Compensated Piezoresistive Strain Sensors," *Rev. Sci Instrum.* 79:054901, 6 pages, published online May 2008.

Lee et al. (2008) "Phase Change and Cooling Characteristics of Microjets Measured using Microcantilever Heaters," *Sens. Actuators A* 147:64-69.

Lee et al. (2007) "Thermal Conduction from Microcantilever Heaters in Partial Vacuum," *J. App Phys.* 101:14906, 6 pages, pub. online Jan. 2007.

Lee et al. "Liquid Operation of Silicon Microcantilever Heaters," *IEEE Sens. J.* 1805-1806, vol. 8, No. 11, Nov. 2008.

Lee et al. (Mar. 15, 2002) "A Microsensor Array with Porous Tin Oxide Thin Films and Microhotplate Dangled by Wires in Air," *Sens. Actuators B Chem.* 83:250-255.

Lee et al. (Dec. 2008) "Differential Scanning Calorimeter Based on Suspended Membrane Single Crystal Silicon Microhotplate," *J. Microelectromechanical Syst.* 17(6):1513-1525.

Li et al. (2008) "Concentrated-Mass Cantilever Enhances Multiple Harmonics in Tapping-Mode Atomic Force Microscopy," *Appl. Phys. Lett.* 92(15):151903, 3 pages.

Lyeo et al. (2004) "Profiling the Thermoelectric Power of Semiconductor Junctions with Nanometer Resolution," *Science.* 816-818, vol. 303, Feb. 2004.

Maali et al. (2006) "Reduction of the Cantilever Hydrodynamic Damping Near a Surface by Ion-Beam Milling," *J AppL Phys.* 99(2):024908, 6 pages, pub.online Jan. 2006.

Mamin, H.J. "Thermal Writing Using a Heated Atomic Force Microscope Tip," *Appl. Phys. Lett.* :433-435, vol. 69, No. 3, Jul. 1996.

Meier et al. (Aug. 2005) "Chemical Warfare Agent Detection Using MEMS-Compatible Microsensor Arrays," *IEEE Sens. J.* :712-725, vol. 5, No. 4.

Melamud "Temperature-compensated high-stability silicon resonators," *Appl. Phys. Lett.* 90: 244107, 3 pages, published online Jun. 2007.

Najafi et al. (Oct. 1994) "A Micromachined Ultra-Thin-Film Gas Detector," *IEEE Trans. Electron. Dev.* :1770-1777, vol. 41, No. 10.

Nelson, B.A. (May 2007) "Nanoscale Thermal Processing Using a Heated Atomic Force Microscope Tip," Ph.D. Dissertation, Georgia Institute of Technology, 169 pages.

Oden "Uncooled Thermal Imaging Using a Piezoresistive Microcantilever," *Appl. Phys. Lett.* 69(21): 3277-3279, Nov. 1996.

Olson et al. The Design and Operation of a MEMS Differential Scanning.

Nanocalorimeter for High-Speed Heat Capacity Measurements of Ultrathin Films, *J. Microelectromech. Syst.* :355-364, vol. 12, No. 3, Jun. 2003.

(Feb. 1, 2005) "Size-Dependent Melting of Bi Nanoparticles," *J. Appl. Phys.* 97:034304, 9 pages, Olson et al.

Pagonis et al. "Fabrication and Testing of an Integrated Thermal Flow Sensor Employing Thermal Isolation by a Porous Silicon Membrane Over an Air Cavity," *J. Micromech. Microeng.* 14:793-797, Apr. 2004.

Park et al. (Apr. 2007) "Frequency-Dependent Electrical and Thermal Response of Heated Atomic Force Microscope Cantilevers," *J. Microelectromech. Syst.* 16(2):213-222.

Park et al. "Routine Femtogram-Level Chemical Analyses Using Vibrational Spectroscopy and Self-Cleaning Scanning Probe Microscopy Tips," *Anal. Chem.* :3221-3228, vol. 80, No. 9, May 2008.

Park et al. (2007) "Low Temperature Characterization of Heated Microcantilevers," *J. Appl. Phys.* 101:094504, 9 pages.

Pinnaduwage et al. (Nov. 2004) "A Sensitive, Handheld Vapor Sensor Based on Microcantilevers," *Rev. Sci. Instrum.* 75(11):4554-4557.

Privorotskaya et al. "Silicon Microcantilever Hotplates with High Temperature Uniformity," *Sens. Act. A* 152:160-167, Mar. 2009.

Rabe et al. "Vibrations of Free and Surface-Coupled Atomic Force Microscope Cantilevers: Theory and Experiment," *Rev. Sci. Instrum.* 67(9):3281-3293, Sep. 1996.

Rabe et al. (2000) "Quantitative Determination of Contact Stiffness Using Atomic Force Acoustic Microscopy," *Ultrasonics* 38(1-8):430-437.

Ravi (Nov. Dec. 1991) "Oxidation Sharpening of Silicon Tips," *J. Vac. Sci. Technot B.* :2733-2737, vol. 9, No. 6.

Reggiani et al. (2002) "Electron and Hole Mobility in Silicon at Large Operating Temperatures —Part I: Bulk Mobility," *IEEE Trans Electron Dev.* 49:490-499, vol. 49, No. 3.

Remmert et al. (Oct. 2007) "Contact Potential Measurement Using a Heated Atomic Force Microscope Tip," *Appl. Phys. Lett.* 91(14):143111, 3 pages.

Remmert (May 2007) "Nano Thermal and Contact Potential Analysis with Heated Probe Tips," M.S. Dissertation, Georgia Institute of Technology, 62 pages.

Rinaldi et al. (2008) "Frequency Tuning AFM Optical Levers Using a Slot," *Microsyst. Technol.* 14(3):361-369, published online Nov. 2007.

Rinaldi et al. (2007) "Tuning the Dynamic Behavior of Cantilever MEMS Based Sensors and Actuators," *Sens. Rev.* 27(2):142-150.

Sadewasser et al. (2006) "Modified Atomic Force Microscopy Cantilever Design to Facilitate Access of Higher Modes of Oscilllation," *Rev. Sci Instrum.* 77:073703, 5 pages.

Sadewasser (2006) "Special Cantilever Geometry for the Access of Higher Oscillation Modes in Atomic Force Microscopy," *Appl. Phys. Lett.* 89(3):3, 3 pages.

Sahin et al. (2004) "High-Resolution Imaging of Elastic Properties Using Harmonic Cantilevers," *Sens. Actuators a: Physical* 114(2-3):183-190, availableOnline2-04.

Sberveglieri et al. (Aug. 1997) "Silicon Hotplates for Metal Oxide Gas Sensor Elements, " *Microsyst. Tech.* 3:183-190.

Semancik et al. (1998) "Kinetically Controlled Chemical Sensing Using Micromachined Structures," *Acc. Chem. Res.* :279-287, vol . 31, No . 5, pub. on Web May 1998.

Sheehan et al. (Aug. 30, 2004) "Nanoscale Deposition of Solid Inks via Thermal Dip Pen Nanolithography," *Appl. Phys. Lett.* 85(9):1589-1591.

Sheng et al. (Jun. 25, 1998) "A Low-Power CMOS Compatible Integrated Gas Sensor Using Maskless Tun Oxide Sputtering," *Sens. Actuators B. Chem.* 49:81-87.

Shirke et al. (May-Jun. 2007) "Femtomolar Isothermal Desorption Using Microhotplate Sensors," *J. Vac. Sci. Technol.* A:514-526, vol. 25, No. 3.

Solzbacher et al. (2003) "A Comprehensive Analytical and Numerical Analysis of Transient and Static Micro Hotplate Characteristics," In; *Transducers '03*, the 12$^{th}$ international Conference on Solid State Sensors, Actuators and Microsystems, Boston, : 1856-1859, conference held Jun. 2003.

Solzbacher et al. (Jun. 10, 2000) "A Modular System of SiC-Based Microhotplates for the Application in Metal Oxide Gas Sensors," *Sens. Actuators B Chem.* 64:95-101.

Spannhake et al. (2007) "$SnO_2$: Sb —A New Material for High-Temperature MEMS Heater Applications: Performance and Limitations," *Sens Actuators B Chem.* 124:421-428, available online Jan. 2007.

Sprunt et al. (Sep. 1997) "Simultaneous FT-Raman Differential Scanning Calorimetry Measurements Using a Low-Cost Fiber-Optic Probe," *Appl. Spectrosc.* :1410-1414, vol. 51, No. 9.

Stark "Optical Lever Detection in Higher Eigenmode Dynamic Atomic Force Microscopy," *Rev. Sci. Instrum.* 75(11):5053-5055 Nov. 2004.

Stark et al. "Tapping-Mode Atomic Force Microscopy and Phase-Imaging in Higher Eigenmodes," *Appl. Phys. Lett.* 74(22):3296-3298, May 1999.

Suehle et al. (Mar. 1993) "Tin Oxide Gas Sensor Fabricated Using CMOS Micro-Hotplates and in situ Processing," *IEEE Electeron Dev. Lett.* 118-120, vol .14, No. 3.

Szoszkiewicz et al. (2007) "High-Speed, Sub-15 nm Feature Size Thermochemical Nanolithography," *Nano Lett.* 1064-1069, vol. 7, No . 4, pub. on Web Mar. 2007.

Thundat et al. (Feb. 1, 1995) "Vapor Detection Using Resonating Microcantilevers," *Anal. Chem.* 67(3):519-521.

Tsamis et al. (Oct. 15, 2003) "Thermal Properties of Suspended Porous Silicon Micro-Hotplates for Sensor Applications," *Sens. Actuators B Chem.* 95:78-82.

Udrea et al. (Aug. 30, 2001) "Design and Simulations of SOICMOS Micro-Hotplate Gas Sensor," *Sens. Actuators B Chem.* 78:180-190.

Unal et al. (2007) "Nanoscale Quantitative Stress Mapping with Atomic Force Microscopy," *Appl. Phys. Lett.* 90: 113111, 3 pages, pub. online Mar. 2007.

Unal et al. (2006) "Ultrafast Molecule Sorting and Delivery by Atomic Force Microscopy," *Appl. Phys. Lett.* 88: 183105, 3 pages, pub. online May 2006.

Varesi et al. "Scanning Joule Expansion Microscopy at Nanometer Scales," *Appl. Phys. Lett.* 72(1)37-39, Jan. 1998.

Vettiger et al. "The 'Millipede' —Nanotechnology Entering Data Storage," *IEEE Trans. Nanotechnol.* 1:39-55, vol . 1, No. 1, Mar. 2002.

Washburn et al. "Micro-Flame Ionization Detection Using a Catalytic Micro-Combuster," *IEEE Sensors* :322-325, Mar. 2005.

Wiche et al. (Sep. 23, 2005) "Thermal Analysis of Silicon Carbode Based Micro Hotplates for Metal Oxiede Gas Sensors," *Sens. Actuators A. Phys.* 123-124:12-17.

Williams et al (1986) "Scanning Thermal Profiler," *Appl. Phys. Lett.* 49(23):1587-1589, Dec.

Wu et al. "Bioassay of Prostate-Specific Antigen (PSA) using Microcantilevers," *Nat. Biotechnol.* 19:856-860 , Sep. 2001.

Zeyen et al. "Design and test of a novel higher harmonic imaging AFM probe with a dedicated second cantilever for harmonic amplification," Transducers and Eurosensors '07—14th International Conference on Solid-State Sensors, Actuators and Microsystems :1545-1548, Jun. 2007.

Zeyen et al. (2008) "Preamplifying cantilevers for contact resonance mode imaging," Solid-State Sensors, Actuators, and Microsystems Workshop, Hilton Head Island, South Carolina, Jun. 1-5, :44-47.

Zeyen et al. "Preamplifying Cantilevers for Dynamic Atomic Force Microscopy," *Appl. Phys. Lett.*, 94:103507, 3 pages, Mar. 2009.

Zhang et al. (2006) "A Micro-Pirani Vacuum Gauge Based on Microhotplate Technology," *Sens. Actuators A* 126:300-305, available online Nov. 2005.

Zhang et al. (Aug. 2007) "Nanoscale Calorimetry Using a Suspended Bridge Configuration," *J. Microelectromech Syst.* :861-871, vol. 16, No. 4.

Zhang et al. (Oct. 15, 2000) "Size-Dependent Melting Point Depression of Nanostructures: Nanocalorimetric Measurements," *Phys. Rev. B. Condens Matter* :10548-10557 , vol. 62, No. 15.

Zhang et al. (Jan. 17, 2005) "Thermal Characterization of Liquids and Polymer Thin Films Using a Microcalorimeter," *Appl. Phys. Lett.* 86(3):034101.

Zhong et al. (1993) "Fractured Polymer Silica Fiber Surface Studied by Tapping Mode Atomic-Force Microscopy," *Surf. Sci.* 290(1-2):L688-L692.

\* cited by examiner (a)

(b)

MICROCANTILEVER HEATER-THERMOMETER WITH INTEGRATED TEMPERATURE-COMPENSATED STRAIN SENSOR

STATEMENT REGARDING FEDERALLY SPONSORED RESEARCH OR DEVELOPMENT

This invention was made with government support under Subcontract No. B552749 to the Regents of the University of California and Georgia Tech Research Corporation under United States Government Prime Contract No. W-7405-RNG-48 represented by the Department of Energy National Nuclear Security Administration (DOE/NNSA) for the management and operation of Lawrence Livermore National Laboratory (LLNL). The government has certain rights in the invention.

CROSS REFERENCE TO RELATED APPLICATION

Not Applicable.

BACKGROUND OF THE INVENTION

This invention is in the field of atomic force microscopes and micro-cantilevers. This invention relates generally to a microcantilever having a temperature compensating piezoresistive strain sensor and integrated heater-thermometer. This invention also relates to methods of using such a cantilever in the fields of thermodynamic measurements and chemical/biochemical sensing.

Since the invention of the atomic force microscope (AFM), microcantilevers have become one of the most frequently used microelectromechanical systems (MEMS) devices with applications ranging from scanning probe microscopy to bio/chemical sensing. Microcantilevers are often functionalized by introducing current traces, piezoresistive or piezoelectric materials to realize specific applications. Heatable microcantilevers having either doped single-crystalline or polycrystalline silicon or patterned metal traces allow current flow so that they can be heated by means of resistive (Joule) heating. This heating in microcantilevers can be used for bimorph actuation, thermomechanical data storage, thermal displacement sensing in contact and tapping modes, novel nano-material synthesis, nanoscale thermal analysis and nanoscale thermal manufacturing. Recently, cantilever type micro-hotplates have been reported as an alternative platform for calorimetry. A cantilever type micro-hotplate fabricated based on silicon technology has been introduced and several microcantilever hotplates were designed, fabricated, and characterized to investigate response time and temperature uniformity.

Microcantilevers with integrated piezoresistive strain sensors are mainly used to replace optical deflection sensing but are also employed in various sensing applications such as gas flow sensing, acceleration sensing, microjet measurements and bio/chemical sensing. Especially as bio/chemical sensors, piezoresistive microcantilevers are often prepared with a selective coating sensitive to a specific analyte. Analyte adsorption induces static deflection by creating a surface stress, and thus embedded piezoresistors can measure analyte adsorption.

Microcantilevers having both resistive heaters and piezoresistors can offer simultaneous heating and deflection sensing. These hybrid types have been used as multi-functional scanning probes in thermomechanical data storage. Similarly, microcantilevers with the ability of independent heating and sensing operation that have high sensitivity to surface stress could be used for a variety of sensor applications. One example would be calorimetry of a material adhered to the cantilever surface. Chemical processes such as melting and evaporation and chemical reactions between substances could be triggered by the heaters while the changes in the surface stresses on the cantilever are monitored and can give information about the material or reaction properties. Other examples include biochemical sensing, where one might wish to interrogate the temperature-dependence of biochemical binding to a microcantilever.

One strategy for suppressing unwanted signals, such as temperature drift, in piezoresistive cantilever sensors is to fabricate cantilever pairs for a differential measurement. Two microcantilevers with identical piezoresistive strain gauges can be arrayed closely and interfaced in a Wheatstone bridge to cancel temperature drift with the assumption they have the same temperature progression. However, this approach would not be appropriate for cases in which the two cantilevers experience different temperatures. This could be the case when a reactive coating modifies the thermal properties of one cantilever. Temperature deviations between the two devices can also be caused by the system environment, e.g. by thermal gradients due to gas flow directions. On-chip temperature compensation for piezoresistive cantilever sensors has been demonstrated, but these cantilevers did not have integrated heater-thermometers. Furthermore, all previous approaches to on-chip temperature compensation use the principle of a Wheatstone bridge circuit on the cantilever, a method which assumes unidirectional, equal stress in all resistors. However, for chemical sensing, in which a reactive layer causes a surface stress on the silicon surface, the stress distribution in the cantilever is complex and three-dimensional. Therefore, it is favorable to incorporate independent sensors for stress and temperature in the cantilever to correct the effect of thermal variations on the mechanical signal.

SUMMARY OF THE INVENTION

The present invention provides microcantilever hotplate devices which incorporate temperature compensating strain sensors into a cantilever structure. The devices of the present invention comprise microcantilevers having temperature compensating strain sensors and resistive heaters. In an embodiment, the devices of the present invention are useful as microhotplates and are capable of heating a material, compound, or species which is bound to or provided on the microhotplate surface. The present invention also provides methods for using a microcantilever hotplate for temperature compensated surface stress measurements, chemical/biochemical sensing, measuring various properties of compounds adhered to the microcantilever hotplate surface, or for temperature compensated deflection measurements.

In an exemplary embodiment, a microhotplate of the present invention comprises a cantilever having a fixed end and a free end; a pair of piezoresistive sensors integrated into the cantilever near the fixed end, wherein the first piezorestive sensor is aligned along a first crystal axis of the cantilever and has a first piezoresistive coefficient, and wherein the second piezoresistive sensor is aligned along a second crystal axis of the cantilever and has a second piezoresistive coefficient that is less than said first piezoresistive coefficient; and a heater-thermometer integrated into the cantilever. In a preferred embodiment the second piezoresistive coefficient is very small (i.e. less than or equal to 1% of the first piezoresistive coefficient). As used herein, the expression "piezoresistive sensors integrated into the cantilever near the fixed end" refers to a relative position of the piezoresistive sensors between 0 and 200 μm of the cantilever fixed end, preferably for some applications between 0 and 50 μm of the fixed end of the cantilever. This expression also includes embodiments where the piezoresistive sensors are spatially coincident with the fixed end of the cantilever.

In an embodiment preferred for some applications, the present invention provides a method of sensing a surface stress of a microhotplate. A method of this aspect comprises the steps of providing a microhotplate of the present invention having a pair of piezoresistive sensors, electrically connecting the first and second piezoresistive sensors in a Wheatstone bridge circuit or other circuit capable of sensing a change in a resistance, and sensing a change in a resistance of one of the piezoresistive sensors, thereby sensing a surface stress in the microhotplate. In a preferred embodiment of this method, the piezoresistive sensors are electrically connected in the Wheatstone bridge circuit or resistance sensing circuit in an arrangement which compensates for a change in the resistances of the piezoresistive sensors due to temperature. In another preferred embodiment, the piezoresistive sensors are positioned near the fixed end of a cantilever of the microhotplate in proximity to each other, such that they have a substantially identical temperature. In some embodiments the first and second piezoresistive sensors are positioned less than 10 μm, 25 μm, 50 μm, 100 μm, or 250 μm from one another In another embodiment preferred for some applications, the present invention provides a method of sensing a property of a compound, species, or substance. A method of this aspect comprises the steps of providing a microhotplate of the present invention having a pair of piezoresistive sensors positioned near the fixed end of a microcantilever and a heater-thermometer positioned in the free end of the microcantilever; contacting the free end of the microcantilever with a compound, species, or substance; providing a voltage or current to the heater-thermometer to affect a temperature change in the microcantilever and compound, species, or substance and wherein such a temperature change produces a surface stress in the microcantilever; and sensing a change in a resistance of at least one of the piezoresistive sensors. This method may also further comprise sensing the resistance of the heater-thermometer to allow for determination of the temperature of the cantilever and compound, species, or substance. In an embodiment, the change in resistance of a piezoresistive sensor is sensed by electrically connecting one or both piezoresistive sensors in a Wheatstone bridge circuit, for example in a manner to compensate for a change in the resistances of the piezoresistive sensors due to temperature.

Useful properties that are capable of being sensed by the methods of the present invention include, but are not limited to: a melting point of the compound, species, or substance; a boiling point of the compound, species, or substance; a binding energy of the compound, species, or substance; a heat capacity of the compound, species, or substance; a mechanical expansion of the compound, species, or substance; a mechanical contraction of the compound, species or substance; or other properties. In some embodiments, a surface stress produced in the microcantilever may be produced by a specific event occurring or at a specific temperature. Such events include, but are not limited to: a change in the state of the compound, species, or substance, for example melting or boiling; a reduction in the amount of the compound, species, or substance present on the microcantilever, for example caused by evaporation; a change in the extent of binding of the compound, species or substance to the microcantilever, for example a reduction in binding from 100% of the initial amount of compound, species or substance bound to a percentage less than 100% of the initial amount bound; a mechanical expansion of the compound, species, or substance; a mechanical contraction of the compound, species or substance; or other events.

In an alternative embodiment, the present invention provides a method for sensing a species bound to a microhotplate. A method of this aspect comprises the steps of: providing a first microhotplate of the present invention having a pair of piezoresistive sensors positioned near the fixed end of a microcantilever and a heater-thermometer positioned in the free end of the microcantilever; providing a species capable of binding to the free end of the cantilever, wherein the binding of the species to the cantilever produces a surface stress in the cantilever; and sensing a change in a resistance of at least one of the piezoresistive sensors, thereby sensing the species bound to the microhotplate. The method may further comprise the step of providing a voltage or current to the heater-thermometer to affect a change in the temperature of or fix the temperature of the microcantilever. In a preferred embodiment, the free end of the cantilever comprises a substance capable of selectively binding the species of interest. In a preferred embodiment, the change in resistance of a piezoresistive sensor is sensed by a method comprising electrically connecting one or both piezoresistive sensors in a Wheatstone bridge circuit, preferably in a manner to compensate for a change in resistance of the piezoresistive sensors due to temperature.

In another embodiment, the method of sensing a species bound to a microhotplate may further comprise the steps of: providing a second microhotplate of the present invention substantially identical to the first microhotplate; providing the second microhotplate in an environment substantially identical to that of the first microhotplate, wherein the environment of the second microhotplate does not have the species of interest present; and electrically connecting the piezoresistive sensors of the first and second microhotplates in a Wheatstone bridge circuit in a manner that compensates for changes in resistance of the piezoresistive sensors due to effects other than binding of the species to the microcantilever.

The present invention also provides a method of performing a temperature compensated deflection measurement. A method of this aspect comprises the steps of: providing a microhotplate of the present invention having a pair of piezoresistive sensors positioned near the fixed end of a microcantilever and a heater-thermometer positioned in the free end of the microcantilever; electrically connecting the piezoresistive sensors in a Wheatstone bridge circuit in a manner to compensate for a change in the resistance of the piezoresistive sensors due to temperature; and sensing a change in the resistance of at least one of the piezoresistive sensors due to a deflection of the free end of the microcantilever. This method may further comprise providing a voltage or current to the heater-thermometer to change or fix the temperature of the microcantilever.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

"Heater-thermometer" refers to a resistive material which is capable of both generating heat and use as a means for measuring temperature. In an embodiment, a heater-thermometer is a thermistor. An ideal heater-thermometer is a material that has a resistance which is temperature dependent. Providing a current or voltage to a heater-thermometer can result in an increase in the temperature of the heater-thermometer through resistive (Joule) heating. Since the resistance of a heater-thermometer is temperature dependent, it can be used as means for measuring the temperature; i.e., by measuring the resistance of the heater-thermometer, the temperature can be determined. A heater-thermometer useful with some embodiments of the present invention comprises doped silicon, for example silicon doped with phosphorus or boron.

"Piezoresistive sensor" refers to a resistive material having resistance which changes when a strain is induced in the material, for example when the material is stretched or compressed. A piezoresistive sensor useful with some embodiments of the present invention comprises doped silicon, for example silicon doped with phosphorus or boron. In some embodiments of the present invention, piezoresistive sensors are integrated into a cantilever near the fixed end, and are useful for sensing surface stresses induced in the cantilever. According to this aspect, when a surface stress is induced in a cantilever which has an integrated piezoresistive sensor, the resistance of the piezoresistive sensor will change and can be sensed by a resistance sensing circuit thereby sensing the surface stress of the cantilever.

Figure 9:
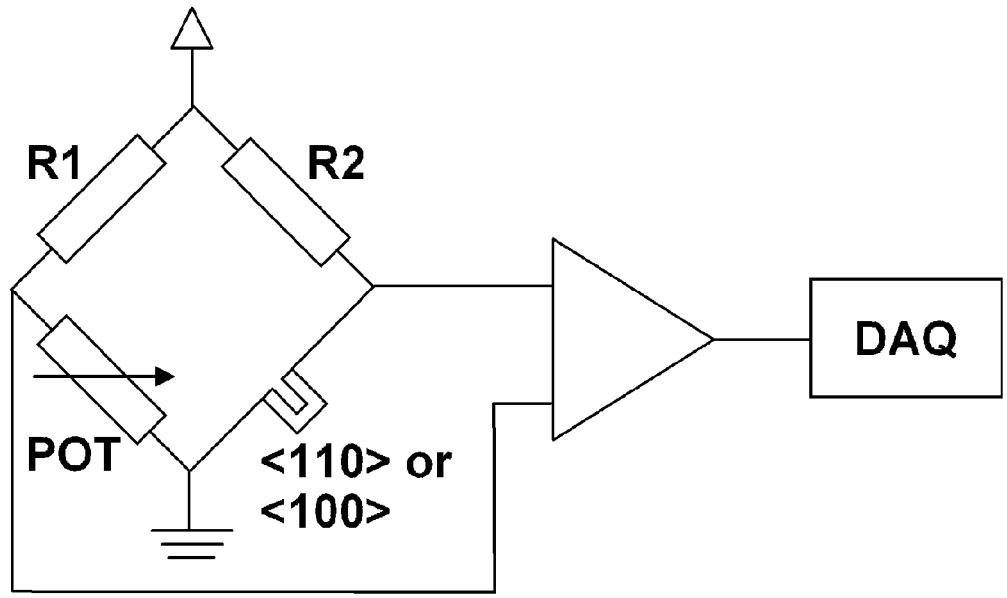
FIG. 9 shows two circuit configurations using the on-chip resistors in the Wheatstone bridge.
Figure 9:
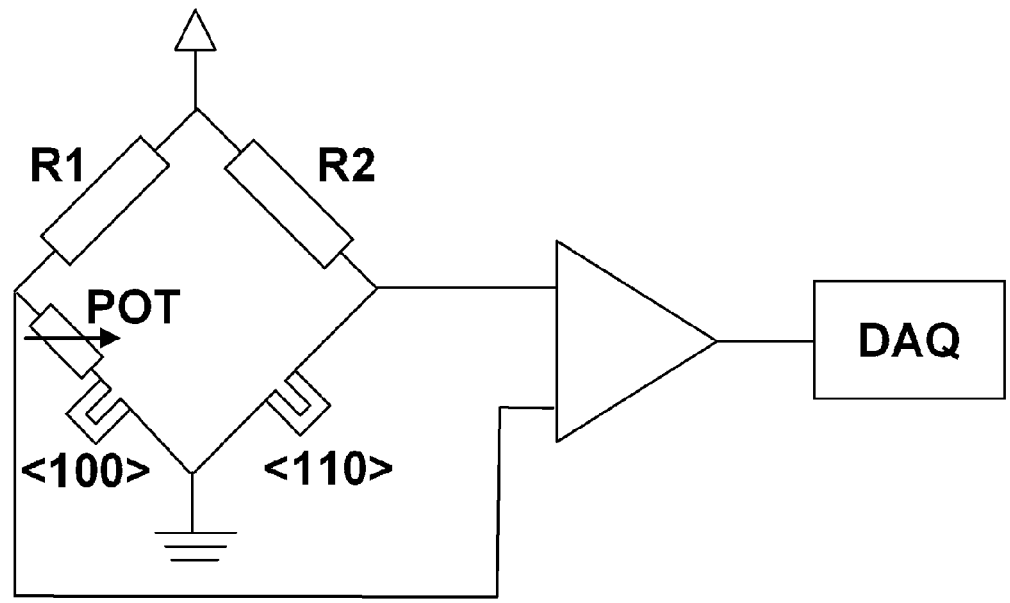

"Wheatstone bridge" refers to an electric circuit which is capable of sensing a change in a resistance of an element of an electric circuit and/or capable of determining an unknown resistance of an element of an electric circuit. Generally, a Wheatstone bridge circuit is constructed by positioning four resistors in a bridge circuit, where one the resistance of one resistor is unknown and the resistance of another resistor is finely adjustable. FIG. 9 shows construction of two different embodiments of Wheatstone bridge circuits useful in the present invention. FIG. 9(a) depicts a Wheatstone bridge circuit in which the resistance of a piezoresistive sensor, for example positioned along a <110> or <100> crystal axis, is being sensed; FIG. 9(b) depicts a Wheatstone bridge circuit in which the resistance of a piezoresistive sensor positioned along a <110> crystal axis is being sensed in reference to a piezoresistive sensor positioned along a <100> crystal axis. The Wheatstone bridge circuit embodied in FIG. 9(b) is useful for compensating for the change of resistance of piezoresistive sensors due to temperature and determining the change of resistance of a piezoresistive sensor due to strain. A Wheatstone bridge similar to that of FIG. 9(b) can also be used for compensating for changes in resistance due to other effects.

"Cantilever" and "microcantilever" are used interchangeably herein and refer to a structure having one fixed or attached end and one free or unattached end, for example a cantilever of an atomic force microscope. In some embodiments, the cantilevers of the present invention have dimensions on the order of 10 to 1000 µm.

"Microhotplate" refers to a microcantilever having a resistive heater or heater-thermometer integrated into at least a portion of the free end of the microcantilever such that the microcantilever can be used to heat a material, species, or compound bound to or positioned on the microcantilever free end. A microhotplate is preferred to have a uniform temperature distribution across the free end of the microcantilever, and may have one or more resistive heater portions. The terms "microhotplate" and "microcantilever hotplate" are used interchangeably herein.

"Thermal communication" refers to an orientation or position of two elements, such as a heater-thermometer and a piezoresistive sensor, such that there is more efficient transfer of heat between the two elements than if isolated or thermally insulated. Elements may be considered in thermal communication if heat is transported between one element and another more quickly than if the elements were isolated or thermally insulated. Two elements in thermal communication may reach thermal equilibrium and in some embodiments may be considered to be constantly at thermal equilibrium with one another.

"Substantially identical" refers to two objects, values, or other items being the same or nearly the same.

The microhotplate devices of the present invention comprise a cantilever having a fixed end and a free end; a pair of piezoresistive sensors integrated into the cantilever near the fixed end, wherein the first piezoresistive sensor is aligned along a first crystal axis of the cantilever and has a first piezoresistive coefficient, and wherein the second piezoresistive sensor is aligned along a second crystal axis of the cantilever and has a second piezoresistive coefficient that is less than the first piezoresistive coefficient; and a heater-thermometer integrated into the cantilever.

In a preferred embodiment, the first piezoresistive coefficient has a value selected from the range of 0.01 to 100Ω per µm of cantilever deflection. In another embodiment, the second piezoresistive coefficient has a very small value, preferably selected from the range of 0 to 1Ω per µm of cantilever deflection. It is also preferred that the first and second piezoresistive sensors are positioned in the cantilever close to one another such that they have a substantially identical temperature, for example a temperature within 1° C., 5° C., 10° C., or 25° C. of one another. In some embodiments, the first and second piezoresistive sensors are positioned less than 10 µm, 25 µm, 50 µm, 100 µm, or 250 µm from one another. In an embodiment, the two piezoresistive strain sensors are positioned near the fixed end of a cantilever, such that they experience a maximum strain when the cantilever is deflected. In an embodiment, the piezoresistive strain sensors are positioned at a distance from the fixed end less than 50% of the total length of the cantilever. In some embodiments, the first and second piezoresistive sensors are positioned less than 10 µm, 25 µm, 50 µm, 100 µm, or 250 µm from the fixed end of the cantilever.

In a preferred embodiment, the microcantilever is comprised of single-crystal silicon or poly-crystalline silicon. In a preferred embodiment, the first piezoresistive sensor is aligned along a first crystal axis of the cantilever and the second piezoresistive sensor is aligned along a second crystal axis of the cantilever. It is also preferred that the first crystal axis is a <110> direction in silicon and the second crystal axis is a <100> direction in silicon. In an embodiment, the piezoresistive sensors comprise doped silicon, preferably silicon doped with an element that is soluble in silicon and that modifies the silicon electronic properties, such as boron or phosphorous. It is also preferred that the piezoresistive sensors have a dopant concentration selected from the range of $10^{14}$ to $10^{20}$ dopants per cubic centimeter.

In a preferred embodiment, the first and second piezoresistive sensors are substantially identical; that is, they have substantially identical compositions and substantially identical dimensions. Substantially identical piezoresistive sensors help to ensure that any changes in the resistance of the piezoresistive sensors due to temperature will be substantially identical. It is preferred that the first and second piezoresistive sensors are identical.

In an alternative embodiment, the microhotplate devices of the present invention may also comprise a resistance sensing circuit electrically connected to the first and second piezoresistive sensors. An exemplary resistance sensing circuit comprises a Wheatstone bridge circuit. Such a Wheatstone bridge circuit can be useful for compensating for changes in the resistances of the first and second piezoresistive sensors due to temperature and for sensing changes in resistance due to surface stresses or cantilever deflections.

In an embodiment, the heater-thermometer of the microhotplate devices of the present invention comprise doped silicon, preferably silicon doped with an element that is soluble in silicon and that modifies the silicon electronic properties, such as boron or phosphorous. It is also preferred that the heater-thermometer regions have a dopant concentration selected from the range of $10^{14}$ to $10^{20}$ dopants per cubic centimeter. In some embodiments the heater-thermometer is positioned either near the free end or near the fixed end of the cantilever. In other embodiments, the heater-thermometer comprises substantially an entire surface area of the cantilever. In exemplary embodiments, the heater-thermometer is partitioned among several regions of the cantilever. In other embodiments, the cantilever and/or heater-thermometer may have any shape, including shapes selected from the group consisting of square, rectangular, circular, U-shaped, ladder shaped, or any other shape into which the cantilever and/or heater-thermometer can be formed or patterned.

The microhotplates devices of the present invention may also comprise other regions of doped silicon or regions of metal, useful as electrical traces or contacts or useful for delivering current to the heater-thermometer regions of the microhotplate. Use of highly doped silicon is preferred for some embodiments because it is capable of carrying high current densities, for example densities capable of producing temperatures in the heater-thermometer regions up to 1300° C.

In an exemplary embodiment, the first and second piezoresistive sensors are in thermal communication with the heater-thermometer of the cantilever. Having the piezoresistive sensors in thermal communication with the heater-thermometer ensures that the temperature of the piezoresistive sensors can be controlled by the heater-thermometer and that the piezoresistive sensors can have substantially identical temperatures.

The invention may be further understood by the following non-limiting example.

EXAMPLE 1

Microcantilever Hotplates with Temperature-Compensated Piezoresistive Strain Sensors This example describes the design, fabrication, and characterization of microcantilever hotplates having both a resistive heater and temperature-compensated a piezoresistive strain gauge. The heater was defined near the cantilever free end and the piezoresistive strain gauges were integrated near the clamped base. To realize temperature compensation, a pair of identical piezoresistors was defined in close proximity. One piezoresistor was aligned to the <110> crystal direction where the piezoresistive coefficient is maximized and the other one was aligned to the <100> crystal direction where the piezoresistive coefficient was nearly zero. The fabricated devices exhibit excellent temperature compensation, with a 20 times reduction in temperature sensitivity. The deflection sensitivity shifted 10% for heating up to 200° C. and cantilever deflection on the order of 10 µm. This work enables cantilever sensors that can measure temperature-dependant phenomena.

Introduction

Since the invention of the atomic force microscope (AFM), microcantilevers have become one of the most frequently used microelectromechanical systems (MEMS) devices with applications ranging from scanning probe microscopy to bio/chemical sensing. Microcantilevers are often functionalized by introducing current traces, piezoresistive or piezoelectric materials to realize specific applications. Heatable microcantilevers having either doped single-crystalline or polycrystalline silicon or patterned metal traces allow current flow so that they can be heated by means of Joule heating. This heating in microcantilevers can be used for bimorph actuation, thermomechanical data storage, thermal displacement sensing in contact and tapping modes, novel nano-material synthesis, nanoscale thermal analysis and nanoscale thermal manufacturing. Recently, cantilever type micro-hotplates have been reported as an alternative platform for calorimetry. A cantilever type micro-hotplate fabricated based on porous silicon technology has been introduced and several microcantilever hotplates were designed, fabricated, and characterized to investigate response time and temperature uniformity.

Microcantilevers with integrated piezoresistive strain sensors are mainly used to replace optical deflection sensing but are also employed in various sensing applications such as gas flow sensing, acceleration sensing, microjet measurements and bio/chemical sensing. Especially as bio/chemical sensors, piezoresistive microcantilevers are often prepared with a selective coating sensitive to a specific analyte. Analyte adsorption induces static deflection by creating a surface stress, and thus embedded piezoresistors can measure analyte adsorption.

Microcantilevers having both resistive heaters and piezoresistors can offer simultaneous heating and sensing. These hybrid types have been used as multi-functional scanning probes in thermomechanical data storages or calorimetry and microbalance applications where the integrated piezoresistors were usually optimized for free-end deflection by a point load and not for surface stress loading. Similarly, microcantilevers with the ability of independent heating and sensing operation that have high sensitivity to surface stress could be used for a variety of sensor applications. One example would be calorimetry of a material adhered to the cantilever surface. Chemical processes such as melting and evaporation and chemical reactions between substances could be triggered by the heaters while the changes in the surface stresses on the cantilever are monitored and can give information about the material or reaction properties. Other examples include biochemical sensing, where one might wish to interrogate the temperature-dependence of biochemical binding to a microcantilever. Recent work has shown the usefulness of cantilever sensors for temperature-dependent biochemical sensing, although heating was global rather than local, and deflection sensing was performed using far-field optics. Neither the heater nor the deflection sensor was fabricated into the cantilever itself.

One strategy for suppressing unwanted signals, such as temperature drift, in piezoresistive cantilever sensors is to fabricate cantilever pairs for a differential measurement. Two microcantilevers with identical piezoresistive strain gauges can be arrayed closely and interfaced in a Wheatstone bridge to cancel temperature drift with the assumption they have the same temperature progression. However, this approach would not be appropriate for cases in which the two cantilevers experience different temperatures. This could be the case when a reactive coating modifies the thermal properties of one cantilever. Temperature deviations between the two devices can also be caused by the system environment, e.g. by thermal gradients due to gas flow directions. On-chip temperature compensation for piezoresistive cantilever sensors has been demonstrated, but these cantilevers did not have integrated heater-thermometers. Furthermore, all previous approaches to on-chip temperature compensation use the principle of a Wheatstone bridge circuit on the cantilever, a method which assumes unidirectional, equal stress in all resistors. However, for chemical sensing, in which a reactive layer causes a surface stress on the silicon surface, the stress distribution in the cantilever is complex and three-dimensional. Therefore, it is favorable to incorporate independent sensors for stress and temperature in the cantilever to correct the effect of thermal variations on the mechanical signal.

This example describes the design, fabrication, and characterization of microcantilever hotplates with temperature-compensated piezoresistive strain gauges. Two different cantilever designs with the same surface area have integrated heaters along the cantilever edges and a pair of piezoresistors for temperature compensation near the clamped base. The fabricated devices showed successful integration of resistive heaters and piezoresistors and their electrical and thermal behaviors were thoroughly tested. Excellent temperature compensation of the deflection signal was confirmed, such that effect of the heater operation was negligible to the piezoresistive readout. These microcantilever hotplates could enable simultaneous calorimetric and thermogravimetric measurements by operating the heater and the piezoresistor pair together.

Design and Fabrication

Figure 1:
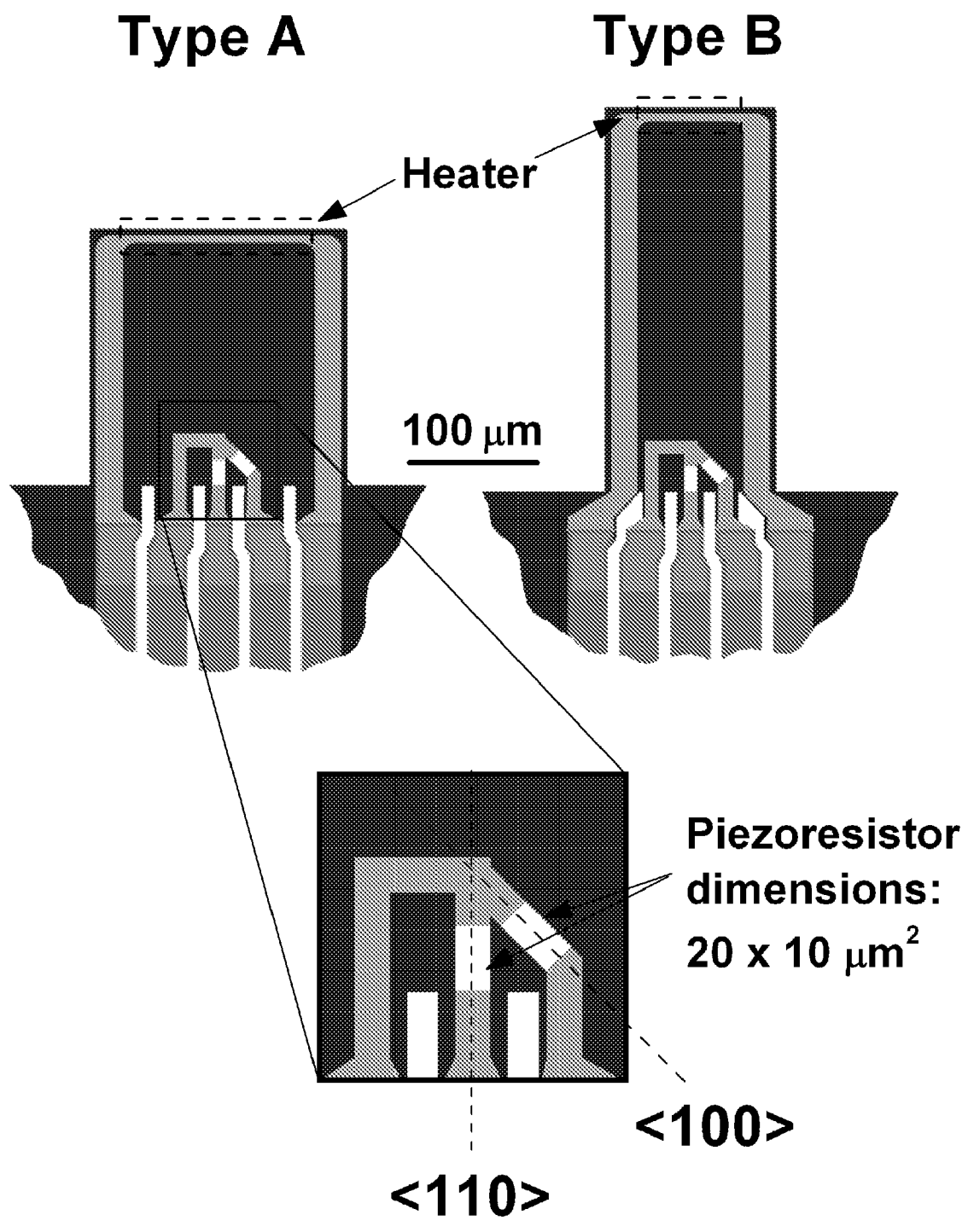
FIG. 1 shows a schematic of two types of microcantilever hotplates with temperature-compensated piezoresistors.

FIG. 1 shows the two cantilever designs. The length and width of cantilever A are each 200 µm, while cantilever B is 300 µm long and 133 µm wide. The two cantilevers have approximately the same surface area. Each cantilever goes through two boron doping procedures, a high doping step to create low-resistance electrical traces, and a low doping step to create high resistance regions for strain and temperature sensing. The specifics of the doping steps are described later. The heater trace is created with the more highly doped silicon, and follows the edge of the cantilever. Both cantilever types have wide current traces on the cantilever edges in length direction and a narrow path at the free end, thus concentrating the majority of the resistance and therefore largest heat generation at the free end. The size of the narrow resistive heater at the free end is 130 µm×5 µm for type A and 63 µm×5 µm for type B. The doped silicon piezoresistor and the temperature-compensating resistor near the cantilever base are made up of the low-doped silicon. The size of each resistor is 20 µm×10 µm as shown in FIG. 1. These elements are connected by highly-doped, lowly resistive electrical traces, so that the resistance of the traces is dominated by the piezoresistors and not the electrical connection.

The temperature compensation is accomplished through two highly resistive elements, one of which being sensitive to both strain and temperature, and the other one being sensitive to temperature but relatively insensitive to strain. The strain-sensing resistive element is the high resistance element on the centerline of the cantilever, such that the current flow direction in the piezoresistor is aligned completely in the highly sensitive <110> crystal direction of the silicon device layer. The second resistor of equal dimensions is placed in close proximity to the first piezoresistor, but with an angle of 45° to it, therefore aligning it to the <100> crystal direction. The piezoresistive coefficients for p-type silicon in this direction are zero, so that the <100> resistor should be insensitive to stresses in the cantilever, whereas the sensitivity of the <110> resistor is maximized. A similar concept has been demonstrated previously for an AFM cantilever with resistors in its two legs, which are angled at 450 to each other and provide effective temperature compensation. To cancel the effect of temperature changes, the two resistors can be connected in one branch of a Wheatstone bridge and supplemented by two additional resistors. For chemical sensing, the other branch of the Wheatstone bridge can be formed by the resistors in a second cantilever on the same chip, thus cancelling effects that alter the surface stress other than those caused by the exposure to the analyte.

Figure 2:
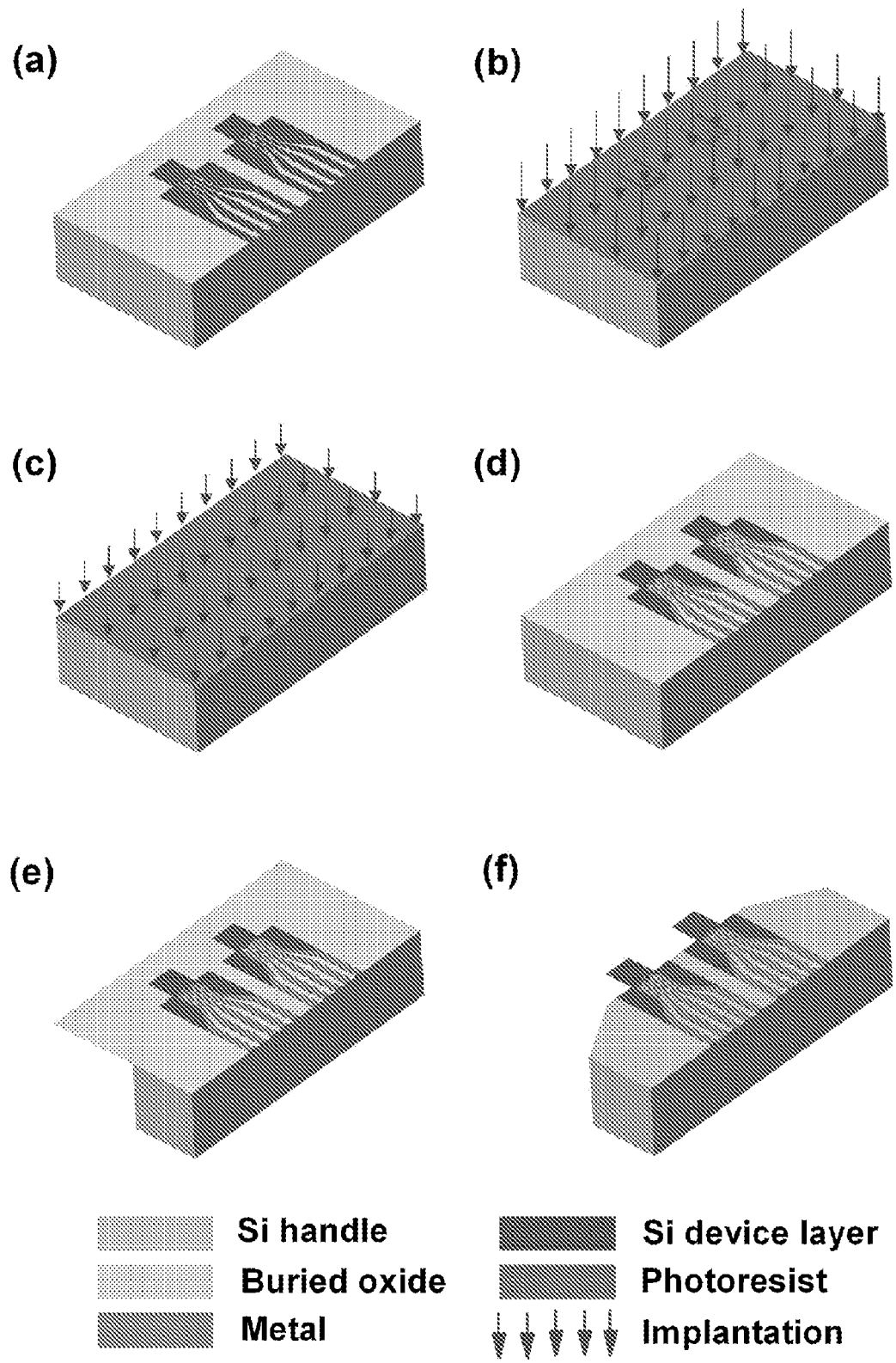
FIG. 2 shows a schematic of six major fabrication processes to make the microcantilever hotplates with temperature-compensated piezoresistors.

FIG. 2 shows the six major fabrication steps to make the microcantilever hotplates with temperature-compensated piezoresistors. The fabrication process started with an n-type silicon-on-insulator (SOI) wafer of orientation <100>, where the silicon device layer was 2 µm, the buried oxide (BOX) layer was 1 µm, and the silicon handle layer was 400 µm. To precisely control the cantilever thickness, silicon dioxide was thermally grown on the wafer surface and etched away with high selectivity. This process, which slowly but evenly consumes the silicon of the device layer, was repeated several times while the remaining device layer thickness was monitored and the growth parameters were adjusted accordingly. After the thinning of the device layer to meet the target thickness of 1 µm, the beam structures were patterned with photoresist (Shipley 1827) and etched into the silicon device layer using a Bosch process in an inductively coupled plasma (ICP) etcher.

Figure 3:
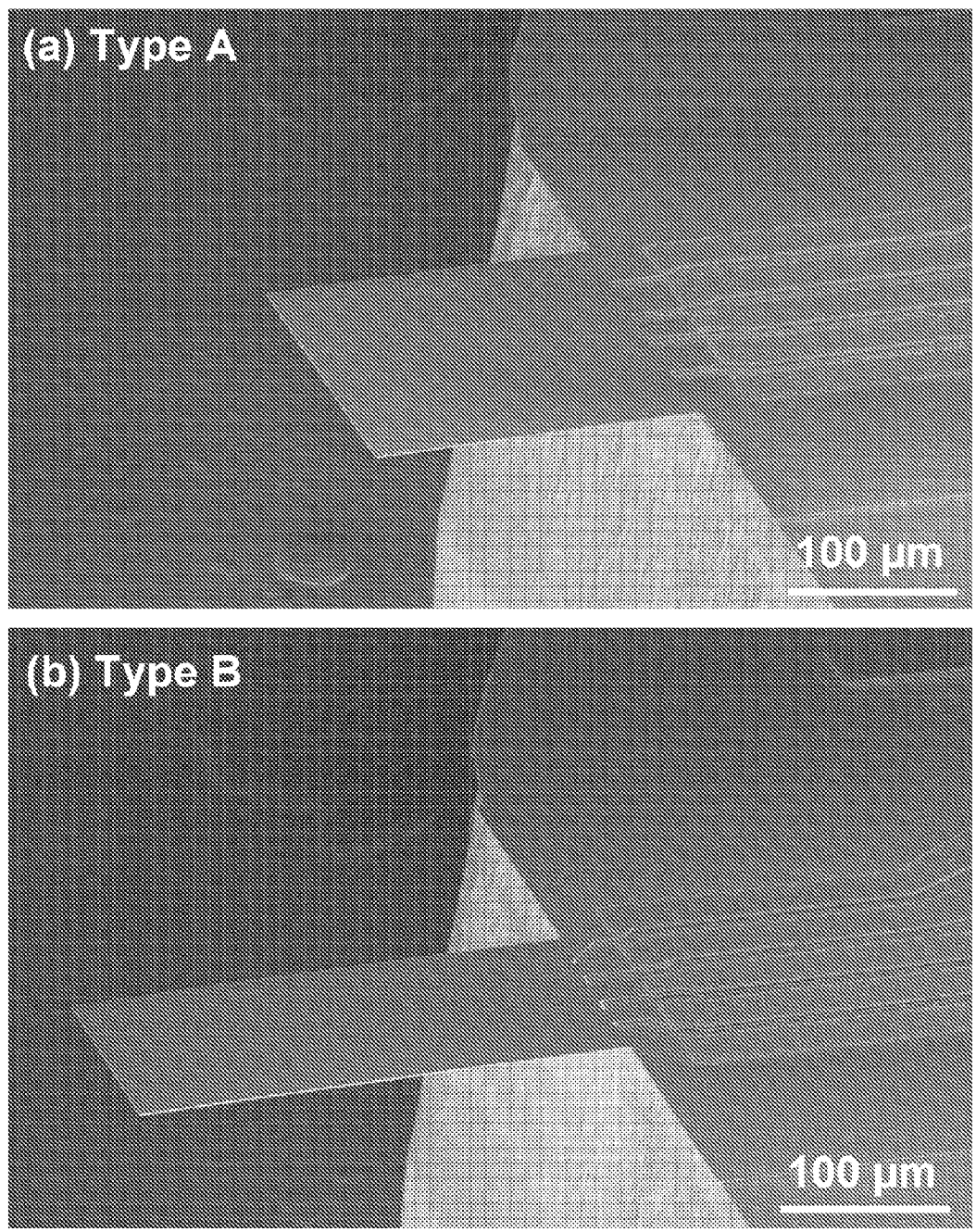
FIG. 3 shows scanning electron micrographs of the fabricated microcantilever hotplates.

Two implantation steps were performed with hard-baked positive photoresist (Shipley 1827) as a mask for ion implantation. The first doping step created current traces and heaters by ion implantation with the parameters shown in Table 1. Then, the photoresist implantation mask was removed and a 200 nm thick layer of silicon dioxide was deposited using plasma enhanced chemical vapor deposition (PECVD) to prevent the dopants from diffusing from silicon to ambient during the subsequent heat treatment. The heat treatment was performed in a furnace with nitrogen atmosphere and is used to anneal the silicon and to achieve a more uniform dopant distribution as shown in FIG. 3. After the heat treatment, the previously deposited silicon dioxide was removed in buffered oxide etch (BOE) to reveal the silicon for the second implantation step. The second doping step was performed to make the piezoresistors by ion implantation with the low doping parameters in Table 1. Similar to the first doping step, a 200 nm thick silicon dioxide was subsequently deposited and the processed wafers were rapid-thermal annealed to recrystallize the silicon structure damaged during ion implantation. The vias connecting the doped silicon to the metal layer were defined with the ICP etcher and aluminum metallization was performed using electron beam deposition in combination with a lift off process. Afterwards, a 30-minute sintering step at 400° C. in a forming gas was done to allow inter-diffusion of doped silicon and aluminum.

TABLE 1

Implantation and heat treatment parameters and expected sheet resistances from doping simulations for high and low-doped areas.

| | High-doped areas | Low-doped areas |
|---|---|---|
| Implantation dose (cm$^{-2}$) | $3 \times 10^{15}$ | $2 \times 10^{13}$ |
| Implantation energy (keV) | 120 | 20 |
| Anneal temperature (° C.) | 1000 | 1000 |
| Anneal time (min) | 60 | 30 |
| Expected sheet resistance (Ω/□) | 32.85 | 2182 |

For the final release, the handle layer was etched from the backside using the Bosch process in the ICP etcher and the BOX layer was removed in 49% hydrofluoric acid (HF). To circumvent the problem that HF attacked the aluminum, an additional photolithography step was added after the backside through-wafer etch. The same lithography mask that revealed the trenches on the backside of the wafer to get free-hanging cantilevers was used again to cover the same geometry on the topside leaving only the cantilever and the surrounding trench area uncovered during the BOX layer etching. This additional step effectively protected the aluminum from the HF and resulted in significantly increased yield. The final yield was better than 90% across the 4-inch wafer. FIG. 3 shows scanning electron micrographs of the released devices.

Simulation

Since the shape and placement of the resistors are fixed by the preceding considerations, the electrical connections between the resistors and to the bond pads are made with highly boron-doped silicon. There are several advantages to using high-doped silicon instead of using the same doping level as for the resistors or using a different electrically conductive material. The resistance of the current traces made of high-doped silicon will be small compared to the resistance of the piezoresistors, which ensures a high ratio of resistance change to initial resistance during sensing operation, and thus a good sensitivity. The high-doped silicon also has a reduced piezoresistive coefficient, so that unwanted resistance change in the conductor areas is small. Furthermore, doping the silicon will have very little effect on the stress state inside the cantilever, whereas deposited layers might cause intrinsic stresses and lead to initial device deformation. Finally, the coefficients of thermal expansion for intrinsic and doped silicon are expected to be very similar, so that changes in the cantilever stress state due to heating are minimized. The last requirement is impossible to achieve with most other electrically conductive materials that could otherwise be used to shape the current paths. The described arrangement of the piezoresistor and the additional resistor is used for both cantilever types.

A design requirement for the piezoresistor, the additional resistor and the heater is that the total resistance for each element is below 5 kΩ. This resistance is sufficiently low to be driven with conventional electronics and to reduce noise, but is high compared to other resistances in the system. Since the two piezoresistors are twice and long as they are wide, the sheet resistance of the low-doped silicon must be below 2.5 kΩ/□. The high doping step must produce electrical connections to the resistors and are small compared to the piezoresistor resistance. The integrated heaters are about 40-50 times longer than they are wide, and so the heaters must be formed by the high doping step.

Figure 4:
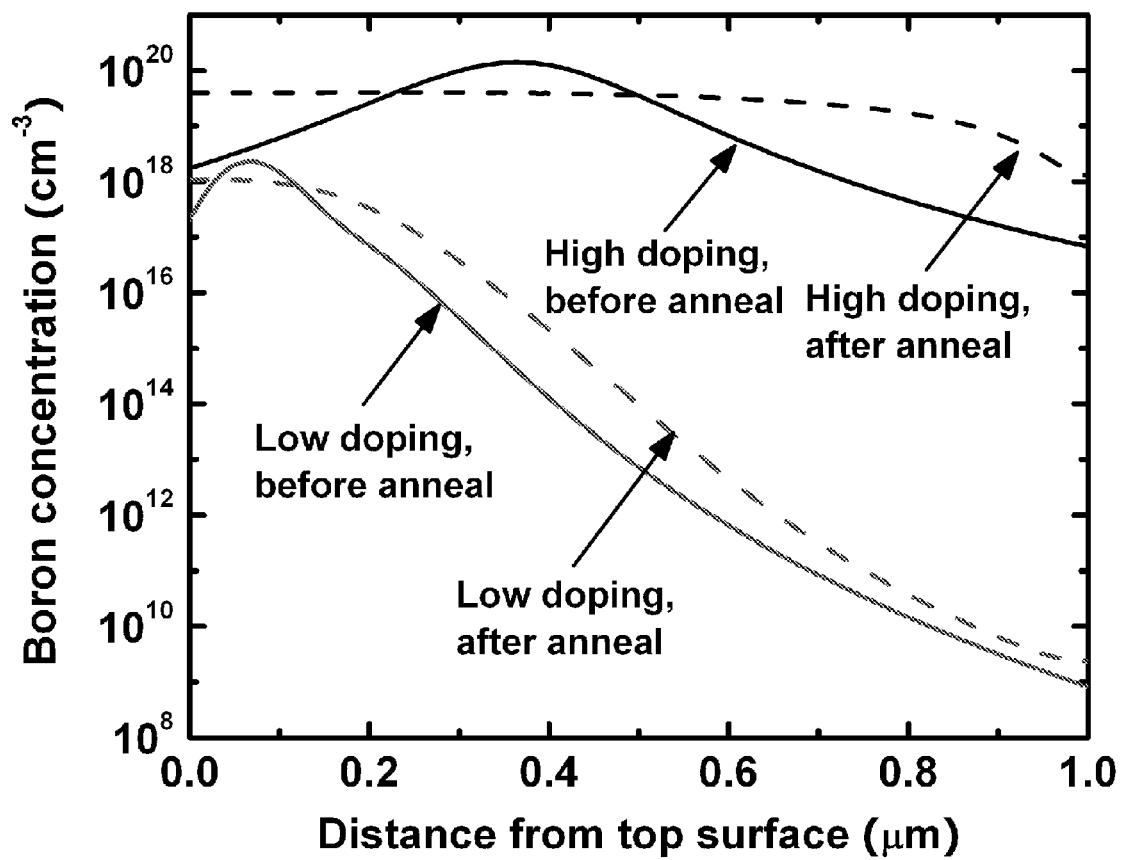
FIG. 4 shows simulated boron concentration using a process simulation tool for low and high doping processes.

FIG. 4 shows the SSUPREME3 simulation results using implantation and heat treatment parameters from Table 1. It can be seen that the low-doped areas have a sheet resistance almost two orders of magnitude higher than that of the high-doped areas. From the expected concentration distribution of the boron atoms, the junction depth of the piezoresistor is about one third of the cantilever thickness. For the high-doped areas that form the connecting traces of the piezoresistor and the additional resistor as well as the heater structures, the dopants are more evenly distributed which acts to reduce current density during heating.

Characterization

Figure 5:
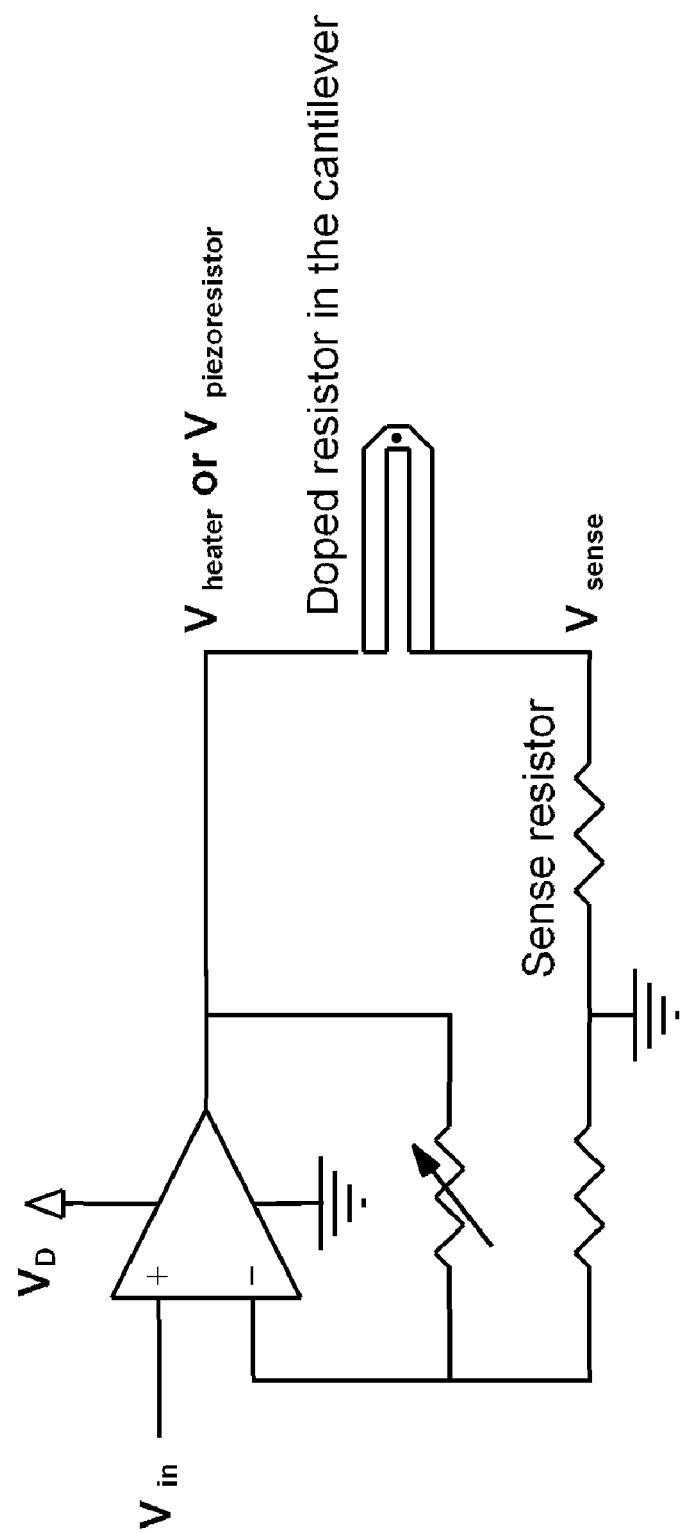
FIG. 5 shows a testing circuit for electrical characterization of the microcantilever hotplates.

Electrical characterization. The basic electrical testing was performed following characterization techniques described in [J. Lee, T. Beechem, T. L. Wright, B. A. Nelson, S. Graham, and W. P. King, J. Microelectromech. Syst., 15 (2006)1644-1655]. FIG. 5 shows the circuit for electrical testing, where the doped resistors (heater, <100> piezoresistor, or <110> piezoresistor) were configured in series with a precision power resistor. The series power resistor can be referred to as the "sense" resistor in the 2-resistor bridge design. FIG. 6(a) shows heater resistances as a function of the applied voltage to the heater (heater voltage). The measured resistances are nearly constant at low voltages since the Joule heating does not increase the device temperature significantly. As the heater voltage is increased, the heater resistance increases due to the positive temperature coefficient of resistance (TCR) at lower temperatures. Once the heater voltage reaches a critical point, the heater resistance drops suddenly. This is the well-known thermal runaway of doped silicon. The sheet resistance of the high-doped areas calculated from the heater resistance and the geometry is between 29 and 32Ω/□, which is very close to the predicted value of 32.85Ω/□.

FIG. 6(b) shows the dissipated power in the heater as a function of the heater voltage. There is a strong increase in power near the thermal runaway as the resistance drops and thus the current increases. The type A cantilever can dissipate more power than the type B cantilever before thermal runaway occurs. This can be attributed to the relatively closer placement of the heater to the silicon handle, which acts as a heat sink.

The same electrical characterization was performed for the piezoresistors in <110> direction and <100> direction, shown in FIGS. 6(c) and (d). The room temperature resistance is very similar for both types and directions, which is expected since the resistor geometries are the same. The alignment of the crystal directions does not affect the resistance, which is important in order to achieve a well-balanced bridge circuit for temperature compensation. Compared to the small surface area of the resistors, the dissipated power in the piezoresistors at the thermal runaway point is very large, which is due to the proximity of the resistors to the clamped base.

The relationship between resistance and voltage in FIGS. 6(a) and (c) and hence also the information about power vs. voltage in FIGS. 6(c) and (d) were obtained after the device was powered past the thermal runaway point several times. These thermal cycles were found to reduce the room temperature resistance and also modify the behavior of the resistance at increased voltages. This burn-in period for heated cantilevers has been previously investigated.

The electrical characteristics of two cantilevers on one chip were within 0.5% from each other, so that only results for one cantilever are shown here. Their similar behaviors make them well-suited for differential operation to cancel out any parasitic effects.

Figure 7:
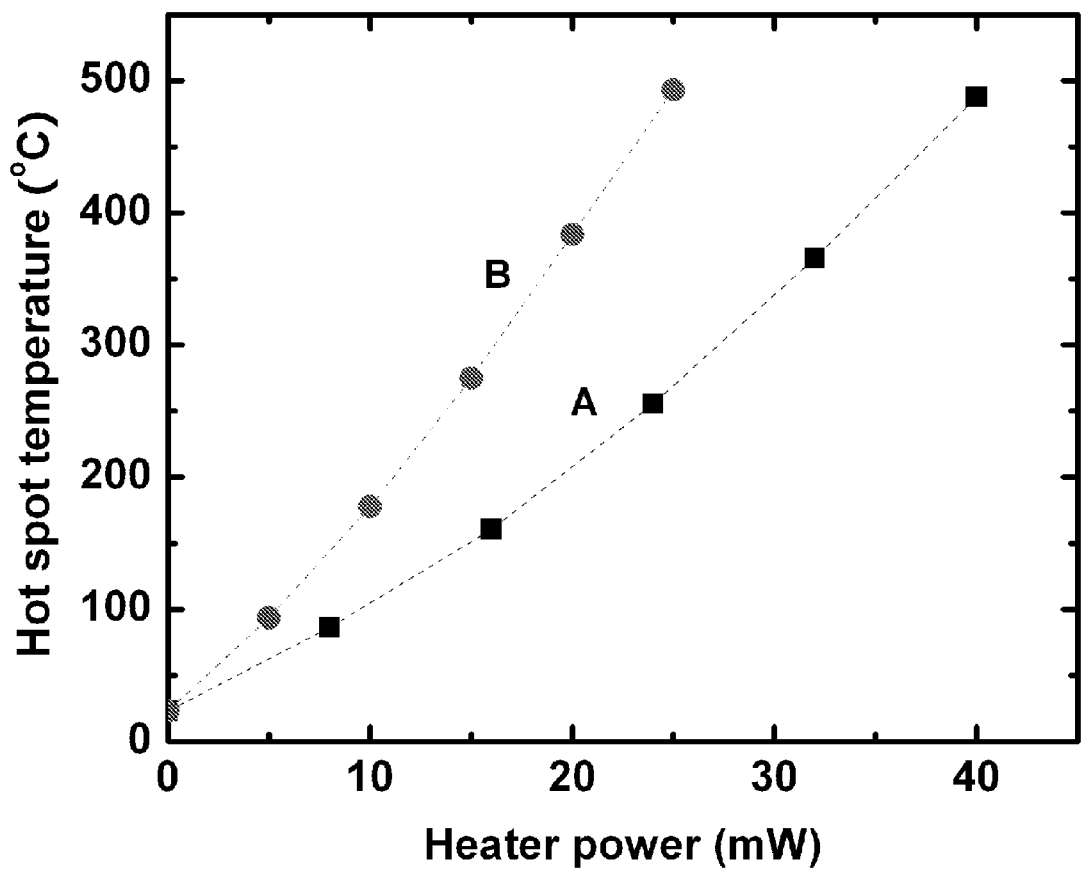
FIG. 7 shows data illustrating the hot spot temperature of each device type for five different power levels from laser Raman thermometry.

Temperature characterization. Raman spectroscopy was used to determine the local temperature in the center of the heater trace at the free end. FIG. 7 shows the hot spot temperature of each device type for five different power levels. The long type B devices reach the same temperatures as type A devices at lower cantilever powers. After the relationship between power and hot spot temperature was determined for each cantilever type the same devices were used to investigate the spatial distribution of the temperature. For this purpose, the power was fixed at a level for which a corresponding hot spot temperature of 200° C. was expected and Raman measurements were taken in eleven different locations along the cantilever length direction between the hot spot and the clamped edge. The temperature distribution is plotted vs. the relative position, i.e. the ratio between distance from the free end and cantilever length, in FIG. 8(a). This plot style was chosen because it allows for a better comparison of the temperature trends of devices with different lengths. Although the distributions are almost linear and very close to each other, there are differences between the two heater shapes. FIG. 8(b), which shows the temperature distribution along the width direction, seems to confirm this trend although the differences are marginal. The data points at about 2.5 and 82.5% in FIG. 8(a) and at 45% in FIG. 8(b) show somewhat higher temperatures than expected from the adjacent data points. Since these positions were in the high-doped silicon areas, the change in the temperature slope could have been caused by the lower thermal conductivity. The deviation could also be caused by the measurement error of the Raman system because the relationship between shift in peak position and temperature is calibrated for the intrinsic silicon. The accuracy of the temperature measurements in the intrinsic silicon areas is within 5 K over the tested temperature range.

Sensitivity characterization. The two cantilevers, whose electrical and thermal properties were characterized in the previous sections, were used to perform deflection sensitivity measurements with the same setup as described in [B. W. Chui, L. Aeschimann, T. Akiyama, U. Staufer, N. F. de Rooij, J. Lee, F. Goericke, W. P. King, and P. Vettiger, Rev. Sci. Instrum., 78 (2007) 043706]. One of the main objectives of these investigations is to quantify the ability to perform temperature compensated deflection measurements using the previously discussed temperature compensation scheme. For this purpose, the characteristics of either the <110> piezoresistor, the <100> piezoresistor, or both piezoresistors were tested during cantilever deflection. These resistors were configured in two Wheatstone bridge circuits, shown in FIG. 9. FIG. 10(a) shows the bridge output as a function of tip deflection for the type B cantilever. As expected, the <100> piezoresistor is very insensitive to cantilever deflection, while the <110> resistor is quite sensitive to cantilever deflection. When both piezoresistors are included in the Wheatstone bridge, the resulting signal is nearly identical to the signal from the <110> resistor alone.

The three experimental runs were repeated, but instead of deflecting the free end of the type B cantilever, the hot spot temperature was modulated by powering the integrated heater trace. FIG. 10(b) shows the bridge output for the heated, undeflected cantilever. For a hot spot temperature of 100° C., the circuit output for the <100> resistor is considerably large. Without temperature compensation, the signal from this piezoresistor is equivalent to a deflection of more than 100 µm. When connected alone, the bridge output signals of the <100> and the <110> resistors are very similar, indicating that their temperature sensitivities are also very similar. When both resistors are connected in the Wheatstone bridge, the output is much smaller because the resistance changes due to the temperature variation cancel. The temperature sensitivity of the temperature-compensation piezoresistor pair is reduced by a factor of 20 compared to the uncompensated piezoresistor configuration at a hot spot temperature of 100° C.

The small signal that remains is assumed to be caused by the difference in the two resistors' average temperature due to their different locations on the cantilever. While only the results from type B are shown, type A cantilever showed similar trends for both tip deflection and temperature modulation. However, the type A cantilever shows higher deflection sensitivity because an equivalent absolute change in cantilever deflection will cause greater stresses in these square-shaped devices than in the longer and narrower type B device. From FIG. 10, it can be concluded that the novel resistor arrangement on the cantilever can indeed be used to measure changes in the cantilever stress with greatly reduced parasitic signals from temperature changes and without sacrificing mechanical sensitivity.

While it is important for the cantilever to be sensitive to deflections with low sensitivity to temperature changes, it is even more important for the cantilever to have consistent deflection sensitivity over a large temperature range. This may be thought of as the temperature coefficient of tip deflection sensitivity (TCS), which must be minimized. FIG. 11(a) shows the temperature-compensated bridge output signal as a function of tip deflection for the type B cantilever. The cantilever was deflected for six different hot spot temperatures under self-heating. The deflection sensitivity is not a very strong function of the hot spot temperature in the range 25-200° C. FIG. 11(b) shows the normalized deflection sensitivities vs. temperature derived from the slope of linear fits to the data points in FIG. 11(a). The slope of the linear fits in the resulting figure represents the TCS and it is on the order of $-5 \times 10^{-4}$ $K^{-1}$. Overall, the deflection sensitivity of the temperature-compensated cantilevers under self-heating varies by about 10% over 200° C. Both cantilever types have very similar values and their difference is not significant compared to the scattering of the data points.

Table 2 summarizes typical characterization results for both cantilever types. Type A has smaller hot spot temperature sensitivity, which indicates that is well-suited for static chemical sensing applications which accompany temperature. However, for oscillatory operation it might be favorable to use the type B cantilever, as the longer cantilever might be more sensitive to adherent mass. The lower hot spot temperature sensitivity of the type A cantilever can be explained with the distance from the piezoresistor pair to the current traces. Due to the short and wide geometry, the type A cantilever has better temperature uniformity specifically for width direction upon the integrated heater operation. The temperature uniformity will likely improve with an optimized heater design.

TABLE 2

Summary of properties for both cantilever types.

|  | A | B |
|---|---|---|
| Room temperature resistance of heater (kΩ) | 1.49 | 1.44 |
| Room temperature resistance of <110> resistor (kΩ) | 3.17 | 3.56 |
| Room temperature resistance of <100> resistor (kΩ) | 3.56 | 3.78 |
| Heater voltage at thermal runaway (V) | 10.8 | 8.1 |
| Heater resistance at thermal runaway (kΩ) | 2.27 | 2.06 |
| Heater power at thermal runaway (mW) | 51.4 | 31.8 |
| Base temperature at 200° C. hot spot temperature (° C.) | 46.2 | 42.9 |
| Room temperature tip deflection sensitivity (mV/V-μm) | 0.268 | 0.0931 |
| Hot spot temperature coefficient of tip deflection sensitivity ($K^{-1}$) | $-5.97 \times 10^{-4}$ | $-5.86 \times 10^{-4}$ |
| Hot spot temperature sensitivity (μV/V-K) | −4.84 | −8.74 |

CONCLUSIONS

Silicon microcantilevers with integrated heater and temperature compensation structures were designed, fabricated, and characterized. Two different cantilever geometries were compared. The hot spot temperatures that can be reached with these devices are greater than 500° C. without thermal failure. The temperature was found to decrease about linearly along the cantilever with the hot spot temperature at the free end and the coldest point at the clamped substrate, while the temperature distribution in the width direction is very uniform. Resistor structures with different crystal directions but in close proximity on the cantilever surface were also implemented in the design and their properties were characterized. The experiments showed that those resistors aligned in <110> direction showed high sensitivity to both cantilever deflection and temperature changes, whereas the resistors in <100> direction were only sensitive to temperature changes and had very little deflection sensitivity. When combined in a Wheatstone bridge circuit, these resistors can greatly reduce temperature-induced error without sacrificing deflection sensitivity. Under temperature compensation, the deflection sensitivity is not a strong function of the temperature, enabling the accurate sensing of deflections during heater operation or exposure to external heat sources.

FIGURE DESCRIPTIONS

FIG. 1 shows a schematic of two types of microcantilever hotplates with temperature-compensated piezoresistors. Their sizes are 200 μm×200 μm (type A) and 300 μm×133 μm (type B), respectively. Thus, both types have approximately the same surface area. There are a resistive heater near the free end and two piezoresistors near the clamped base. The zoom-in shows a piezoresistor parallel to <110> direction and a piezoresistor parallel to <100> direction.

FIG. 2 shows a schematic of six major fabrication processes to make the microcantilever hotplates with temperature-compensated piezoresistors. (a) beam and metal pad outlines are etched into the device layer (b) heater and high doped regions are boron implanted (c) piezoresistors are boron implanted (d) vias are made and aluminum metallization is followed (e) silicon handle layer is etched from the backside using ICP (f) the buried oxide layer is etched in HF.

FIG. 3 shows scanning electron micrographs of the fabricated microcantilever hotplates.

FIG. 4 shows simulated boron concentration using SSU-PREME3 for low and high doping processes. Solid and dashed lines are boron profiles before and after the heat treatment, respectively. From this, the junction depth of the low-doped piezoresistor is about one third of the cantilever thickness. Dopants are more evenly distributed for high-doped areas which acts to reduce current density upon heating.

FIG. 5 shows a testing circuit for electrical characterization. Either doped heater or piezoresistors are connected to a sense resistor (precision power resistor) which senses current and protect the device at high powers. V total represents actual applied voltage to each doped resistor and V sense represents voltage drop across the sense resistor.

Figure 6:
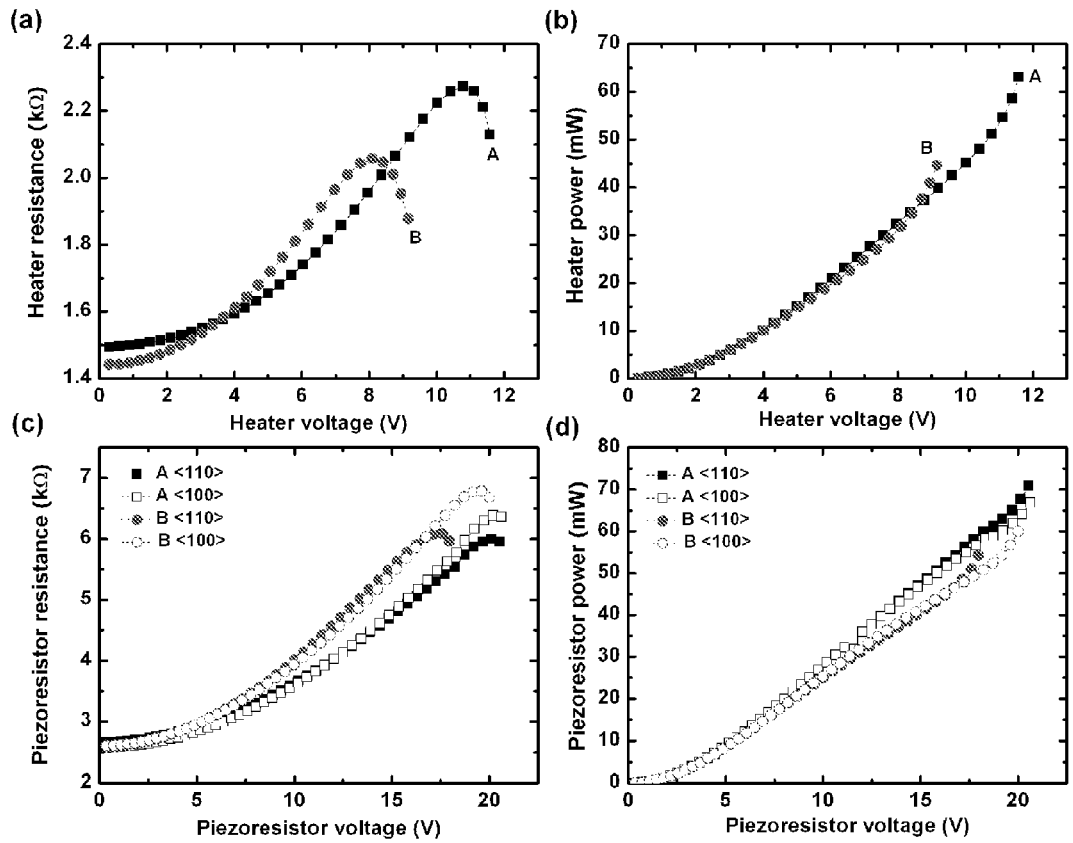
FIG. 6 shows data illustrating (a) Heater resistance and (b) heater power vs. applied voltage to the heater for two cantilever types; (c) Piezoresistor resistance and (d) piezoresistor power vs. applied voltage to the piezoresistors in <110> and <100> direction for two cantilever types.

FIG. 6 shows data illustrating (a) Heater resistance and (b) heater power vs. applied voltage to the heater—heater voltage—for two cantilever types (c) Piezoresistor resistance and (d) piezoresistor power vs. applied voltage to the piezoresistors-piezoresistor voltage—in <110> and <100> direction for two cantilever types.

FIG. 7 shows data illustrating the hot spot temperature of each device type for five different power levels from laser Raman thermometry. The long type B devices reach the same temperatures as type A devices at lower cantilever powers.

Figure 8:
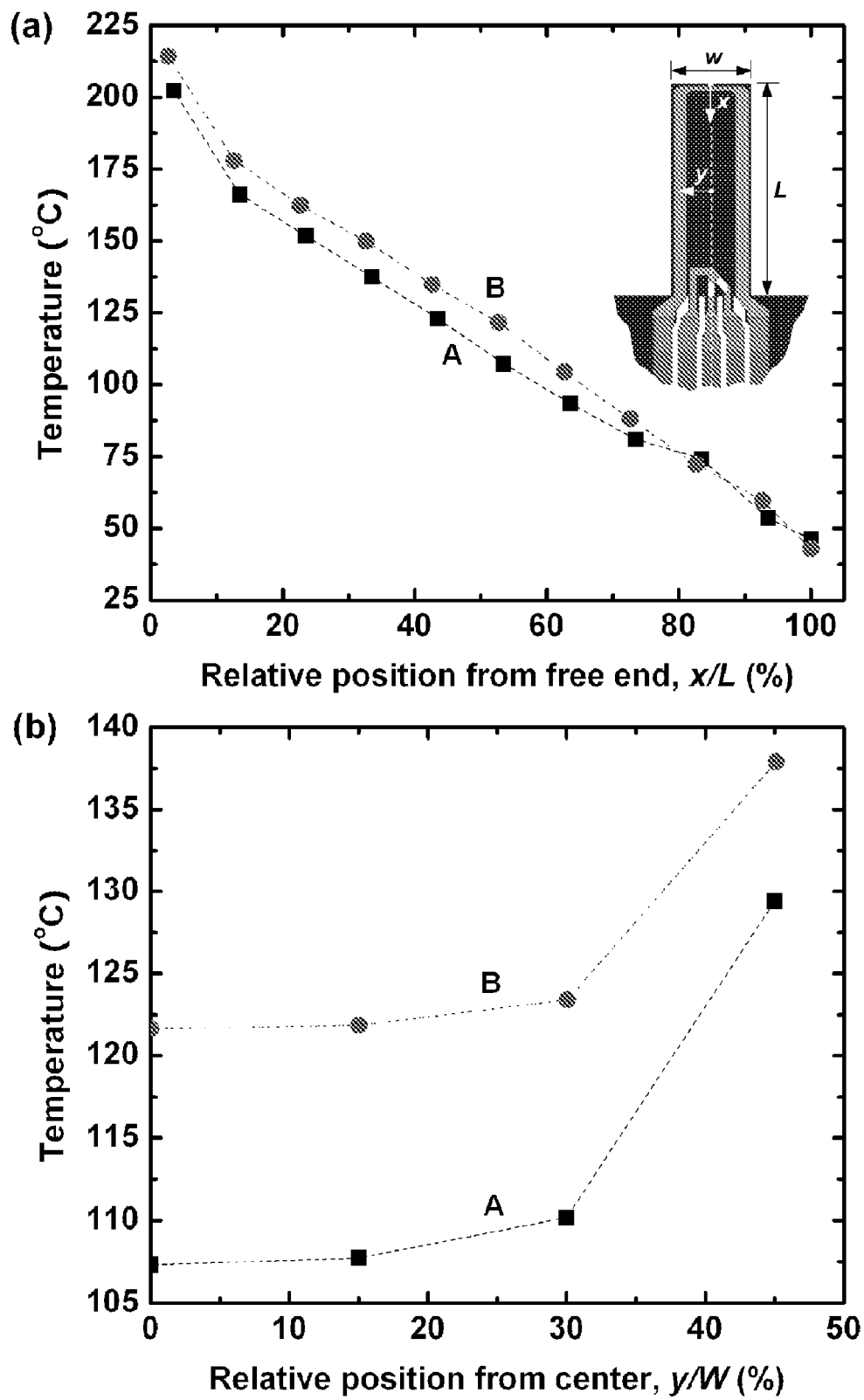
FIG. 8 shows measurements of local temperature vs. relative position for type A and B (a) along the cantilever length, and (b) along the cantilever width.

FIG. 8 shows measurements of local temperature vs. relative position for type A and B (a) along the cantilever length, where 0% is the center of the free end and 100% is the center of the clamped base and (b) along the cantilever width, where 0% is at the cantilever center in length and width direction and 50% is at the edge in width direction and in the center of the length direction.

FIG. 9 shows two circuit configurations using the on-chip resistors in the Wheatstone bridge. (a) To test the individual elements alone, the resistor in either the <110> or the <100> crystal direction was used. (b) To test the compensation characteristics of the resistors, both <110> and <100> crystal direction piezoresistors were used.

Figure 10:
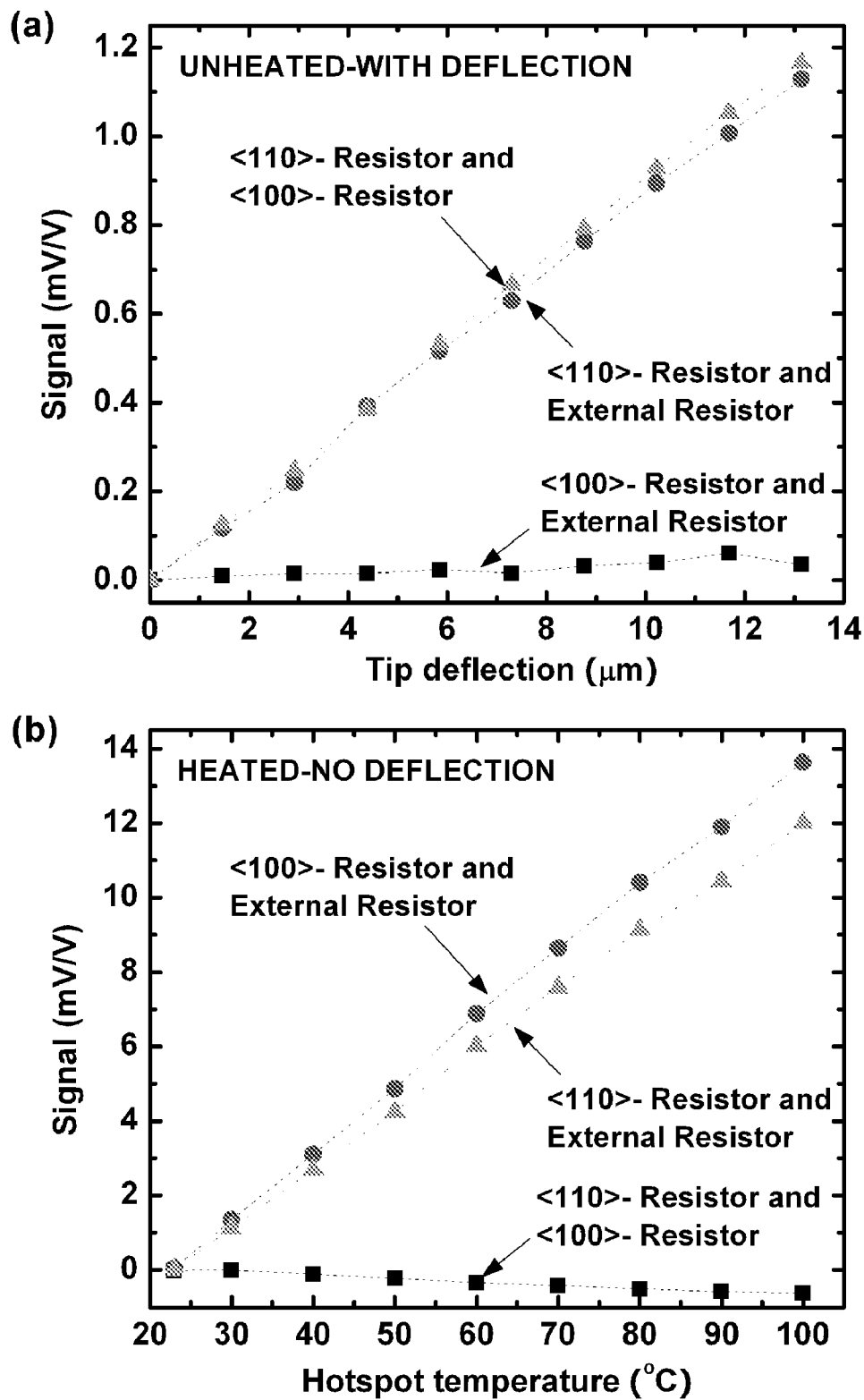
FIG. 10 shows measured characteristics of the various resistors from a type B cantilever.

FIG. 10 shows measured characteristics of the various resistors from a type B cantilever. The bridge output signal is shown for the <110> resistor or the <100> resistor using the circuit in FIG. 9(a), and for both resistors when in the circuit of FIG. 9(b). The bridge output signal is shown for (a) deflection of the unheated cantilever and (b) heating of the cantilever with no deflection. The uncompensated cantilever is sensitive to both temperature and deflection, while the compensated cantilever is sensitive to deflection but relatively insensitive to temperature.

Figure 11:
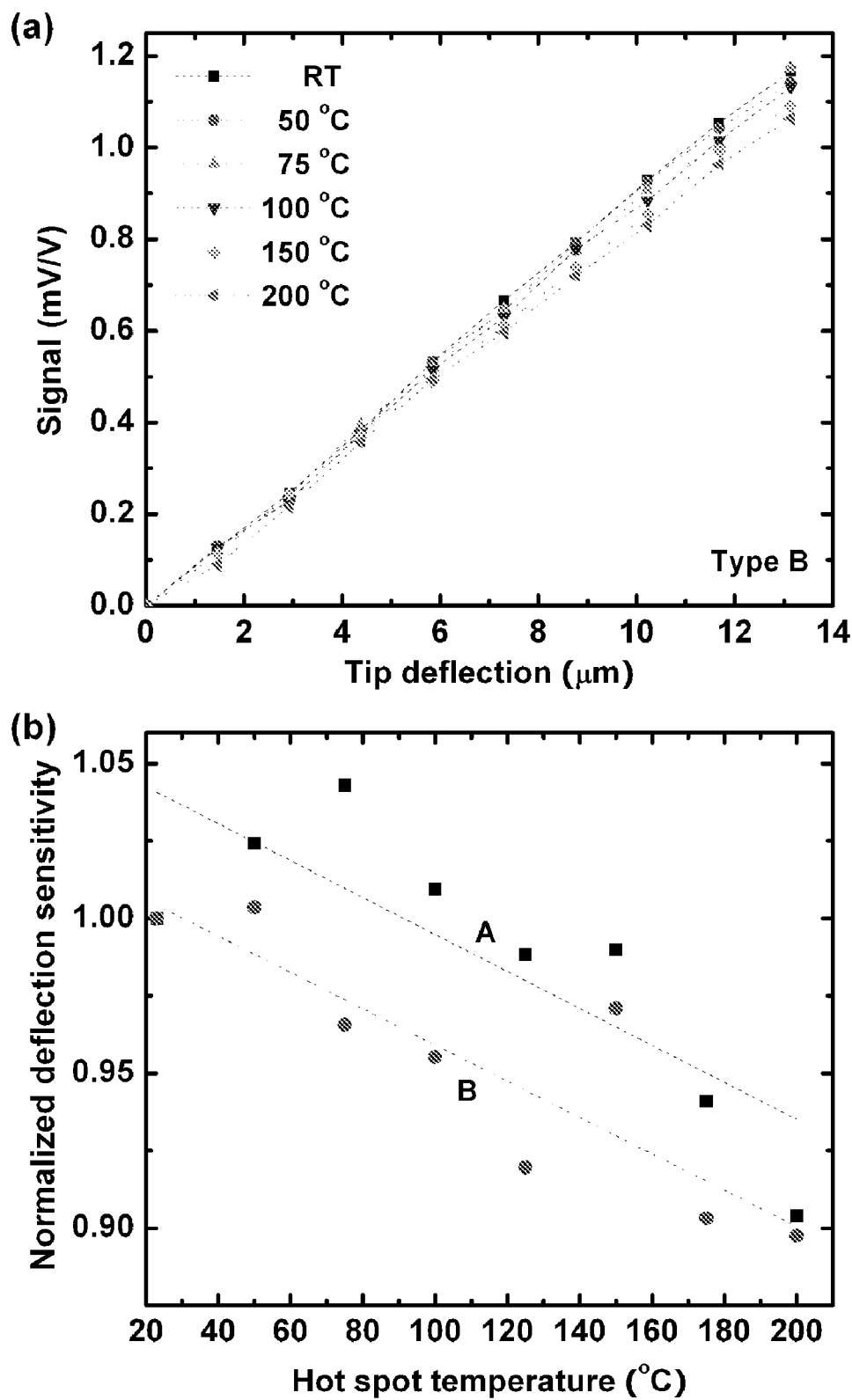
FIG. 11 shows a summary of cantilever deflection sensitivity up to 200° C.

FIG. 11 shows a summary of cantilever deflection sensitivity up to 200° C. (a) Bridge output signal with both piezoresistors configured vs. tip deflection of the type B cantilever for six different hot spot temperatures (b) Normalized tip deflection sensitivity vs. hot spot temperature for both cantilever types. The cantilever deflection sensitivity changes by about 10% over the temperature range measured, which is a factor of 20 improvement over the uncompensated case.

REFERENCES

G. Binnig, C. F. Quate, and C. Gerber, Atomic force microscope, Phys. Rev. Lett., 56 (1986) 930-933.

B. W. Chui, T. D. Stowe, Y. S. Ju, K. E. Goodson, T. W. Kenny, H. J. Mamin, B. D. Terris, and R. P. Ried, Low-stiffness silicon cantilever with integrated heaters and piezoresistive sensors for high-density data storage, J. Microelectromech. Syst., 7 (1998) 69-78.

J. Lee, T. Beechem, T. L. Wright, B. A. Nelson, S. Graham, and W. P. King, Electrical, thermal, and mechanical characterization of silicon microcantilever heaters, J. Microelectromech. Syst., 15 (2006) 1644-1655.

P. A. Rasmussen, J. Thaysen, O. Hansen, S. C. Eriksen, and A. Boisen, Optimised cantilever biosensor with piezoresistive read-out, Ultramicroscopy, 97 (2003) 371-376.

N. Abedinov, P. Grabiec, T. Gotszalk, T. Ivanov, J. Voigt, and I. W. Rangelow, Micromachined piezoresistive cantilever array with integrated resistive microheater for calorimetry and mass detection, J. Vac. Sci. Technol., A, 19 (2001) 2884-2888.

T. Akiyama, U. Staufer, N. F. de Rooij, D. Lange, C. Hagleitner, O. Brand, H. Baltes, A. Tonin, and H. R. Hidber, Integrated atomic force microscopy array probe with metal-oxide-semiconductor field effect transistor stress sensor, thermal bimorph actuator, and on-chip complementary metal-oxide-semiconductor electronics, J. Vac. Sci. Technol., B, 18 (2000) 2669-2675.

R. Pedrak, T. Ivanov, K. Ivanova, T. Gotszalk, N. Abedinov, I. W. Rangelow, K. Edinger, E. Tomerov, T. Schenkel, and P. Hudek, Micromachined atomic force microscopy sensor with integrated piezoresistive, sensor and thermal bimorph actuator for high-speed tapping-mode atomic force microscopy phase-imaging in higher eigenmodes, J. Vac. Sci. Technol., B,21 (2003) 3102-3107.

M. Despont, J. Brugger, U. Drechsler, U. Dürig, W. Häberle, M. Lutwyche, H. Rothuizen, R. Stutz, R. Widmer, H. Rohrer, G. K. Binnig, and P. Vettiger, VLSI-NEMS chip for parallel AFM data storage, Sens. Actuators, A, 80 (2000) 100-107.

W. P. King, T. W. Kenny, K. E. Goodson, G. L. W. Cross, M. Despont, U. Dürig, H. Rothuizen, G. Binnig, and P. Vettiger, Design of atomic force microscope cantilevers for combined thermomechanical writing and thermal reading in array operation, J. Microelectromech. Syst., 11 (2002) 765-774.

K. J. Kim, K. Park, J. Lee, Z. M. Zhang, and W. P. King, Nanotopogrical imaging using a heated atomic force microscope cantilever probe, Sens. Actuators, A, 136 (2007) 95-103.

K. Park, J. Lee, Z. M. Zhang, and W. P. King, Nanotopogrical imaging with a heated atomic force microscope cantilever in tapping mode, Rev. Sci. Instrum., 78 (2007) 043709.

E. O. Sunden, T. L. Wright, J. Lee, W. P. King, and S. Graham, Room-temperature chemical vapor deposition and mass detection on a heated atomic force microscope cantilever, Appl. Phys. Lett., 88 (2006) 033107.

W. P. King, S. Saxena, B. A. Nelson, B. L. Weeks, and R. Pitchimani, Nanoscale thermal analysis of an energetic material, Nano Lett., 6 (2006) 2145-2149.

B. A. Nelson and W. P. King, Measuring material softening with nanoscale spatial resolution using heated silicon probes, Rev. Sci. Instrum., 78 (2007) 023702.

B. A. Nelson, W. P. King, A. R. Laracuente, P. E. Sheehan, and L. J. Whitman, Direct deposition of continuous metal nanostructures by thermal dip-pen nanolithography, Appl. Phys. Lett., 88 (2006) 033104.

R. Triantafyllopoulou, S. Chatzandroulis, C. Tsamis, and A. Tserepi, Alternative micro-hotplate design for low power sensor arrays, Microelectron. Eng., 83 (2006) 1189-1191.

J. Lee and W. P. King, Microcantilever hotplates: Design, fabrication, and characterization, Sens. Actuators, A, 136 (2007) 291-298.

M. Tortonese, R. Barrett, and C. Quate, Atomic resolution with an atomic force microscope using piezoresistive detection, Appl. Phys. Lett., 62 (1993) 834-836.

Y. Su, A. G. R. Evans, A. Brunnschweiler, and G. Ensell, Characterization of a highly sensitive ultra-thin piezoresistive silicon cantilever probe and its application in gas flow velocity sensing, J. Micromech. Microeng., 12 (2002) 780-785.

L. M. Roylance and J. B. Angell, A batch fabricated silicon accelerometer, IEEE Trans. Elec. Dev., 26 (1979) 1911-1917.

J. Lee, K. Naeli, H. Hunter, J. Berg, T. Wright, C. Courcimault, N. Naik, M. Allen, O. Brand, A. Glezer, and W. P. King, Characterization of liquid and gaseous micro- and nanojets using microcantilever sensors, Sens. Actuators, A, 134 (2007) 128-139.

T. Thundat, R. J. Warmack, G. Y. Chen, and D. P. Allison, Thermal and ambient-induced deflections of scanning force microscope cantilevers, Appl. Phys. Lett., 64 (1994) 2894-2896.

T. Thundat, E. A. Wachter, S. L. Sharp, and R. J. Warmack, Detection of mercury-vapor using resonating microcantilevers, Appl. Phys. Lett., 66 (1995) 1695-1697.

A. Boisen, J. Thaysen, H. Jensenius, and O. Hansen, Environmental sensors based on micromachined cantilevers with integrated read-out, Ultramicroscopy, 82 (2000) 11-16.

H. Jensenius, J. Thaysen, A. A. Rasmussen, L. H. Veje, O. Hansen, and A. Boisen, A microcantilever-based alcohol vapor sensor-application and response model, Appl. Phys. Lett., 76 (2000) 2615-2617.

R. Marie, H. Jensenius, J. Thaysen, C. B. Christensen, and A. Boisen, Adsorption kinetics and mechanical properties of thiol-modified DNA-oligos on gold investigated by microcantilever sensors, Ultramicroscopy, 91 (2002) 29-36.

M. Lutwyche, C. Andreoli, G. Binnig, J. Brugger, U. Drechsler, W. Häberle, H. Rohrer, H. Rothuizen, P. Vettiger, G. Yaralioglu, and C. Quate, 5×5 2D AFM cantilever arrays a first step towards a Terabit storage device, Sens. Actuators, A, 73 (1999) 89-94.

Z. X. Yang, Y. Yu, X. X. Li, and H. F. Bao, Nano-mechanical electro-thermal probe array used for high-density storage based on NEMS technology, Microelec. Reliability, 46 (2006) 805-810.

R. Berger, C. Gerber, J. K. Gimzewski, E. Meyer, and H. J. Güntherodt, Thermal analysis using a micromechanical calorimeter, Appl. Phys. Lett., 69 (1996) 40-42.

L. A. Pinnaduwage, A. Gehl, D. L. Hedden, G. Muralidharan, T. Thundat, R. T. Lareau, T. Sulchek, L. Manning, B. Rogers, M. Jones, and J. D. Adams, A microsensor for trinitrotoluene vapour, Nature, 425 (2003) 474-474.

S. L. Biswal, D. Raorane, A. Chaiken, H. Birecki, and A. Majumdar, Nanomechanical detection of DNA melting on microcantilever surfaces, Anal. Chem., 78 (2006) 7104-7109.

S. L. Biswal, D. Raorane, A. Chaiken, and A. Majumdar, Using a microcantilever array for detecting phase transitions and stability of DNA, Clin. Lab. Med., 27 (2007) 163-+.

L. A. Pinnaduwage, D. L. Hedden, A. Gehl, V. I. Boiadjiev, J. E. Hawk, R. H. Farahi, T. Thundat, E. J. Houser, S. Stepnowski, R. A. McGill, L. Deel, and R. T. Lareau, A sensitive, handheld vapor sensor based on microcantilevers, Rev. Sci. Instrum., 75 (2004) 4554-4557.

B. W. Chui, L. Aeschimann, T. Akiyama, U. Staufer, N. F. de Rooij, J. Lee, F. Goericke, W. P. King, and P. Vettiger, Advanced temperature compensation for piezoresistive sensors based on crystallographic orientation, Rev. Sci. Instrum., 78 (2007)043706.

C. Hagleitner, A. Hierlemann, D. Lange, A. Kummer, N. Kerness, O. Brand, and H. Baltes, Smart single-chip gas sensor microsystem, Nature, 414 (2001) 293-296.

M. J. Madou, Fundamentals of microfabrication, CRC Press, Boca Raton, Fla., 1997.

R. Hull and INSPEC (Information service), Properties of crystalline silicon, INSPEC, London, 1999.

B. A. Nelson and W. P. King, Temperature calibration of heated silicon atomic force microscope cantilevers, Sens. Actuators, A (in press) available online doi:10.1016/j.sna.2007.06.008.

M. R. Abel, T. L. Wright, W. P. King, and S. Graham, Thermal metrology of silicon microstructures using Raman spectroscopy, IEEE Trans. Comp. Pack. Tech., 30 (2007) 200-208.

F. Goericke, J. Lee, W. P. King, Microcantilever hotplates with temperature-compensated piezoresistive strain sensors, Sensors and Actuators: A Physical (2007), doi:10.1016/j.sna.2007.10.049.

U.S. Pat. Nos. 5,345,815, 5,386,720 and 7,291,446.

U.S. Patent Application Publication No. US2006/0207317.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," "having," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A microhotplate comprising:
 a. a cantilever having a fixed end and a free end;
 b. a pair of piezoresistive sensors integrated into said cantilever near said fixed end, wherein a first piezorestive sensor is aligned along a first crystal axis of said cantilever and has a first piezoresistive coefficient, and wherein a second piezoresistive sensor is aligned along a second crystal axis of said cantilever and has a second piezoresistive coefficient that is less than said first piezoresistive coefficient; and
 c. a heater-thermometer integrated into said cantilever.

2. The microhotplate of claim 1 wherein said second piezoresistive coefficient has a value selected from the range of 0 to 1 Ω per μm of cantilever deflection.

3. The microhotplate of claim 1 wherein said first piezoresistive coefficient has a value selected from the range of 0.1 to 100 Ω per μm of cantilever deflection.

4. The microhotplate of claim 1 wherein the distance between said fixed end of said cantilever and said piezoresistive sensors is less than 50% of the total length of said cantilever.

5. The microhotplate of claim 1 wherein said first and second piezoresistive sensors are positioned in said cantilever in proximity to each other such that they have a substantially identical temperature.

6. The microhotplate of claim 1 wherein said cantilever comprises single crystal silicon.

7. The microhotplate of claim 6 wherein said first crystal axis is a <110> direction in silicon and said second crystal axis is a <100> direction in silicon.

8. The microhotplate of claim 1 wherein said first and second piezoresistive sensors comprise doped silicon.

9. The microhotplate of claim 8 wherein said piezoresistive sensors are doped with an element selected from the group consisting of phosphorous, boron, and other elements that are soluble in the material of the cantilever and that change the cantilever material properties.

10. The microhotplate of claim 8 wherein said piezoresistive sensors have a dopant concentration selected from the range of $10^{14}$ to $10^{20}$ dopants per cubic centimeter.

11. The microhotplate of claim 1 wherein said first and second piezoresistive sensors have substantially identical dimensions and substantially identical compositions.

12. The microhotplate of claim 1 further comprising a resistance sensing circuit electrically connected to said first and second piezoresistive sensors.

13. The microhotplate of claim 12 wherein said resistance sensing circuit comprises a Wheatstone bridge circuit.

14. The microhotplate of claim 12 wherein said Wheatstone bridge circuit compensates for a change in the resistance of said first and second piezoresistive sensors due to temperature.

15. The microhotplate of claim 1 wherein said heater-thermometer comprises a resistive heater.

16. The microhotplate of claim 1 wherein said heater-thermometer comprises doped silicon.

17. The microhotplate of claim 16 wherein said heater-thermometer is doped with an element selected from the group consisting of phosphorous, boron, and other elements that are soluble in the material of the cantilever and that change the cantilever material properties.

18. The microhotplate of claim 16 wherein said heater-thermometer has a dopant concentration selected from the range of $10^{14}$ to $10^{20}$ dopants per cubic centimeter.

19. The microhotplate of claim 1 wherein said heater-thermometer is positioned at said free end of said cantilever.

20. The microhotplate of claim 1 wherein said heater-thermometer comprises substantially an entire surface area of said cantilever.

21. The microhotplate of claim 1 wherein said heater-thermometer is capable of producing temperatures up to 1300° C. in said cantilever.

22. The microhotplate of claim 1 wherein said first and second piezoresistive sensors are in thermal communication with said heater-thermometer.

* * * * *

UNITED STATES PATENT AND TRADEMARK OFFICE
CERTIFICATE OF CORRECTION

| | | |
|---|---|---|
| PATENT NO. | : 7,928,343 B2 | Page 1 of 1 |
| APPLICATION NO. | : 11/950029 | |
| DATED | : April 19, 2011 | |
| INVENTOR(S) | : King et al. | |

It is certified that error appears in the above-identified patent and that said Letters Patent is hereby corrected as shown below:

In Column 2, line 58, "piezorestive" should be replaced with --piezoresistive--.

In Claim 1, Column 20, line 50, "piezorestive" should be replaced with --piezoresistive--.

Signed and Sealed this
Twelfth Day of July, 2011

David J. Kappos
*Director of the United States Patent and Trademark Office*